(12) United States Patent
Eckhardt et al.

(10) Patent No.: US 7,419,959 B2
(45) Date of Patent: Sep. 2, 2008

(54) D-PYRANOSYL-SUBSTITUTED PHENYL DERIVATIVES, MEDICAMENTS CONTAINING SUCH COMPOUNDS, THEIR USE AND PROCESS FOR THEIR MANUFACTURE

(75) Inventors: Matthias Eckhardt, Biberach (DE); Frank Himmelsbach, Mittelbiberach (DE); Peter Eickelmann, Mittelbiberach (DE); Leo Thomas, Biberach (DE); Edward Leon Barsoumian, Toyonaka (JP)

(73) Assignee: Boehringer Ingelheim International, GmbH, Ingelheim (DE)

( * ) Notice: Subject to any disclaimer, the term of this patent is extended or adjusted under 35 U.S.C. 154(b) by 70 days.

(21) Appl. No.: 11/239,917

(22) Filed: Sep. 30, 2005

(65) Prior Publication Data

US 2006/0074031 A1    Apr. 6, 2006

(30) Foreign Application Priority Data

Oct. 1, 2004    (DE) ............... 10 2004 048 388

(51) Int. Cl.
- *A61K 31/70* (2006.01)
- *A61K 31/351* (2006.01)
- *C07H 7/06* (2006.01)
- *C07D 309/10* (2006.01)

(52) U.S. Cl. ............... 514/23; 514/460; 536/1.11; 549/417; 549/418

(58) Field of Classification Search ............... 514/25; 536/4.1, 17.2
See application file for complete search history.

(56) References Cited

U.S. PATENT DOCUMENTS

| | | | |
|---|---|---|---|
| 6,414,126 B1 * | 7/2002 | Ellsworth et al. | 536/17.2 |
| 6,627,611 B2 * | 9/2003 | Tomiyama et al. | 514/23 |
| 6,774,112 B2 * | 8/2004 | Gougoutas | 514/23 |
| 2003/0114390 A1 | 6/2003 | Washburn et al. | |
| 2005/0209166 A1 | 9/2005 | Eckhardt et al. | |

FOREIGN PATENT DOCUMENTS

| | | |
|---|---|---|
| WO | WO 98/31697 A1 | 7/1998 |
| WO | WO 01/27128 A | 4/2001 |
| WO | WO 02/083066 A2 | 10/2002 |
| WO | WO 03/099836 A1 | 12/2003 |
| WO | WO 2004/052902 A1 | 6/2004 |
| WO | WO 2005/092877 A1 | 10/2005 |

OTHER PUBLICATIONS

Carey and Sundberg, "Advanced Organic Chemistry, Fourth Edition, Part B: Reactions and Synthesis" (2001) Published by Kluwer Academic/Plenum Publishers, pp. 822-830.*
U.S. Appl. No. 11/674,839, filed Feb. 2007, Eckhardt et al.*

* cited by examiner

*Primary Examiner*—Shaojia Anna Jiang
*Assistant Examiner*—Eric S Olson
(74) *Attorney, Agent, or Firm*—David A. Dow; Michael P. Morris; Mary-Ellen M. Devlin

(57) ABSTRACT

D-pyranosyl-substituted phenyls of general formula I

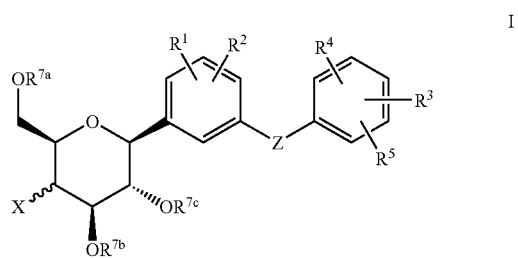

wherein the groups $R^1$ to $R^5$, X, Z and $R^{7a}$, $R^{7b}$, $R^{7c}$ are defined as in claim 1, have an inhibiting effect on the sodium-dependent glucose cotransporter SGLT. The present invention also relates to pharmaceutical compositions for the treatment of metabolic disorders.

28 Claims, No Drawings

US 7,419,959 B2

D-PYRANOSYL-SUBSTITUTED PHENYL DERIVATIVES, MEDICAMENTS CONTAINING SUCH COMPOUNDS, THEIR USE AND PROCESS FOR THEIR MANUFACTURE

This application claims priority to Germany application DE 10 2004 048 388, filed Oct. 1, 2004.

The present invention relates to D-pyranosyl-substituted phenyls of general formula I

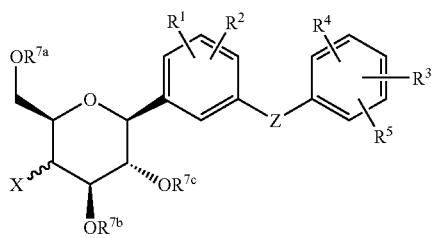

wherein the groups $R^1$ to $R^5$, X, Z and $R^{7a}$, $R^{7b}$, $R^{7c}$ are as hereinafter defined, including the tautomers, the stereoisomers, the mixtures thereof and the salts thereof. The invention further relates to pharmaceutical compositions containing a compound of formula I and the use of a compound according to the invention for preparing a pharmaceutical composition for the treatment of metabolic disorders. The invention also relates to methods of preparing a pharmaceutical composition and a compound according to the invention.

Compounds which have an inhibitory effect on the sodium-dependent glucose cotransporter SGLT are proposed in the literature for the treatment of diseases, particularly diabetes.

Glucopyranosyl-substituted aromatic groups and the preparation thereof and their possible activity as SGLT2 inhibitors are known from published International Patent Applications WO 98/31697, WO 01/27128, WO 02/083066 and WO 03/099836.

The application WO 2004/052902 proposes aromatic fluoroglycoside derivatives as antidiabetics on account of their effect on SGLT. The compounds described by way of example are exclusively O-phenylglycosides.

PROBLEM OF THE INVENTION

The aim of the present invention is to indicate new pyranosyl-substituted phenyls, particularly those which have an effect on the sodium-dependent glucose cotransporter SGLT, particularly SGLT2. A further aim of the present invention is to indicate pyranosyl-substituted phenyls which, by comparison with known structurally similar compounds, have a greater inhibitory effect on the sodium-dependent glucose cotransporter SGLT2 in vitro and/or in vivo and/or have improved pharmacological or pharmacokinetic properties.

Moreover the present invention sets out to provide new pharmaceutical compositions which are suitable for the prevention and/or treatment of metabolic disorders, particularly diabetes.

The invention also relates to a process for preparing the compounds according to the invention.

Further aims of the present invention will immediately become apparent to the skilled man from the remarks above and hereinafter.

OBJECT OF THE INVENTION

In a first aspect the present invention relates to D-pyranosyl-substituted phenyls of general formula I

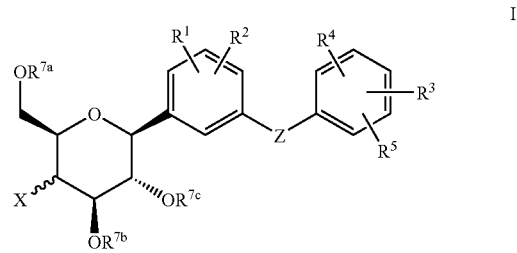

wherein $R^1$ denotes hydrogen, fluorine, chlorine, bromine, iodine, $C_{1-6}$-alkyl, $C_{2-6}$-alkynyl, $C_{2-6}$-alkenyl, $C_{3-10}$-cycloalkyl, $C_{3-10}$-cycloalkyl-$C_{1-3}$-alkyl, $C_{5-10}$-cycloalkenyl, $C_{5-10}$-cycloalkenyl-$C_{1-3}$-alkyl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperazin-1-ylcarbonyl, $C_{1-4}$-alkoxycarbonyl, amino, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$-alkyl)piperazin-1-yl, $C_{1-4}$-alkylcarbonylamino, $C_{1-6}$-alkyloxy, $C_{3-10}$-cycloalkyloxy, $C_{5-10}$-cycloalkenyloxy, aryloxy, $C_{1-4}$-alkylsulphanyl, $C_{1-4}$-alkylsulphinyl, $C_{1-4}$-alkylsulphonyl, $C_{3-10}$-cycloalkylsulphanyl, $C_{3-10}$-cycloalkylsulphinyl, $C_{3-10}$-cycloalkylsulphonyl, $C_{5-10}$-cycloalkenylsulphanyl, $C_{5-10}$-cycloalkenylsulphinyl, $C_{5-10}$-cycloalkenylsulphonyl, arylsulphanyl, arylsulphinyl, arylsulphonyl, hydroxy, cyano or nitro, while alkyl, alkenyl, alkynyl, cycloalkyl and cycloalkenyl groups may be partly or completely fluorinated or may be mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be replaced by CO or $SO_2$, and $R^2$ denotes hydrogen, fluorine, chlorine, bromine, hydroxy, $C_{1-4}$-alkyl, $C_{1-4}$-alkoxy, cyano or nitro, while alkyl groups may be mono- or polysubstituted by fluorine, or in the event that $R^1$ and $R^2$ are bound to two adjacent C atoms of the phenyl ring, $R^1$ and $R^2$ may be joined together such that $R^1$ and $R^2$ together form a $C_{3-5}$-alkylene, $C_{3-5}$-alkenylene or butadienylene bridge, which may be partly or completely fluorinated or may be mono- or disubstituted by identical or different substituents selected from chlorine, hydroxy, $C_{1-3}$-alkoxy and $C_{1-3}$-alkyl, and wherein one or two methylene groups may be replaced independently of one another by O, S, CO, SO, $SO_2$ or $NR^N$, and wherein in the case of a butadienylene bridge one or two methyne groups may be replaced by an N atom, $R^3$ denotes hydrogen, fluorine, chlorine, bromine, iodine, $C_{1-6}$-alkyl, $C_{2-6}$-alkynyl, $C_{2-6}$-alkenyl, $C_{3-10}$-cycloalkyl, $C_{3-10}$-cycloalkyl-$C_{1-3}$-alkyl, $C_{5-10}$-cycloalkenyl, $C_{5-10}$-cycloalkenyl-$C_{1-3}$-alkyl, aryl, heteroaryl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperazin-1-ylcarbonyl, hydroxycarbonyl, $C_{1-4}$-alkoxycarbonyl, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$-alkyl)piperazin-1-yl, $C_{1-4}$-alkylcarbonylamino, arylcarbonylamino, heteroaryl-carbonylamino, $C_{1-4}$-alkylsulphonylamino, arylsulphonylamino, $C_{1-6}$-alkoxy, $C_{3-7}$-cycloalkyloxy, $C_{5-7}$-cycloalkenyloxy, aryloxy, heteroaryloxy, $C_{1-4}$-alkyl-sulphanyl, $C_{1-4}$-alkylsulphinyl, $C_{1-4}$-alkylsulphonyl, $C_{3-10}$-cycloalkylsulphanyl, $C_{3-10}$-cycloalkylsulphinyl, $C_{3-10}$-cycloalkylsulphonyl, $C_{5-10}$-cycloalkenylsulphanyl, $C_{5-10}$-cycloalkenylsulphinyl, $C_{5-10}$-cycloalkenylsulphonyl, arylsulphanyl, arylsulphinyl, arylsulphonyl, amino, hydroxy, cyano or nitro, while alkyl, alkenyl, alkynyl, cycloalkyl- and cycloalkenyl groups may be partly or completely fluorinated or mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be replaced by CO or $SO_2$, and $R^4$ independently of one another denote hydrogen, fluorine, chlorine, bromine, iodine, cyano, nitro, $C_{1-3}$-alkyl, $C_{1-3}$-alkoxy or methyl or methoxy substituted by 1 to 3 fluorine atoms, or if $R^3$ and $R^4$ are bound to two adjacent C atoms of the phenyl ring, $R^3$ and $R^4$ may be joined together such that $R^3$ and $R^4$ together form a $C_{3-5}$-alkylene, $C_{3-5}$-alkenylene or butadienylene bridge, which may be partly or completely fluorinated or mono- or disubstituted by identical or different substituents selected from chlorine, hydroxy, $C_{1-3}$-alkoxy and $C_{1-3}$-alkyl, and wherein one or two methylene groups may be replaced independently of one another by O, S, CO, SO, $SO_2$ or $NR^N$, and wherein in the case of a butadienylene bridge one or two methyne groups may be replaced by an N atom, $R^5$ independently of one another denote hydrogen, fluorine, chlorine, bromine, iodine, cyano, nitro, $C_{1-3}$-alkyl, $C_{1-3}$-alkoxy or methyl or methoxy substituted by 1 to 3 fluorine atoms, and $R^N$ denotes H, $C_{1-4}$-alkyl or $C_{1-4}$-alkylcarbonyl, L are selected independently of one another from among fluorine, chlorine, bromine, iodine, $C_{1-3}$-alkyl, difluoromethyl, trifluoromethyl, $C_{1-3}$-alkoxy, difluoromethoxy, trifluoromethoxy and cyano, $R^{7a}$, $R^{7b}$, $R^{7c}$ independently of one another have a meaning selected from among hydrogen, ($C_{1-18}$-alkyl)carbonyl, ($C_{1-18}$-alkyl)oxycarbonyl, arylcarbonyl and aryl-($C_{1-3}$-alkyl)carbonyl, X denotes hydrogen, fluorine, chlorine, bromine, iodine, $C_{1-6}$alkyl, $C_{2-6}$-alkynyl, $C_{2-6}$-alkenyl, $C_{3-7}$-cycloalkyl-$C_{1-3}$-alkyl, $C_{5-7}$-cycloalkenyl-$C_{1-3}$-alkyl, aryl-$C_{1-3}$-alkyl, heteroaryl-$C_{1-3}$-alkyl, $C_{1-6}$-alkoxy, $C_{2-6}$-alkenyloxy, $C_{2-6}$-alkynyloxy, $C_{3-7}$-cycloalkyloxy, $C_{5-7}$-cycloalkenyloxy, aryloxy, heteroaryloxy, $C_{3-7}$-cycloalkyl-$C_{1-3}$-alkyloxy, $C_{5-7}$-cycloalkenyl-$C_{1-3}$-alkyloxy, aryl-$C_{1-3}$-alkyloxy, heteroaryl-$C_{1-3}$-alkyloxy, aminocarbonyl, $C_{1-4}$-alkylaminocarbonyl, di-($C_{1-3}$-alkyl)aminocarbonyl, hydroxycarbonyl, $C_{1-4}$-alkoxycarbonyl, aminocarbonyl-$C_{1-3}$-alkyl, $C_{1-4}$-alkylaminocarbonyl-$C_{1-3}$-alkyl, di-($C_{1-3}$-alkyl)aminocarbonyl-$C_{1-3}$-alkyl, hydroxycarbonyl-$C_{1-3}$-alkyl, $C_{1-4}$-alkoxycarbonyl-$C_{1-3}$-alkyl, $C_{3-7}$-cycloalkyloxy-$C_{1-3}$-alkyl, $C_{5-7}$-cycloalkenyloxy-$C_{1-3}$-alkyl, aryloxy-$C_{1-3}$-alkyl, heteroaryloxy-$C_{1-3}$-alkyl, $C_{1-4}$-alkylsulphonyloxy, arylsulphonyloxy, aryl-$C_{1-3}$-alkylsulphonyloxy or cyano, while a methylene group directly linked to the pyranose ring may be replaced by $NR^N$, S, CO, SO or $SO_2$, and alkyl, alkenyl, alkynyl, cycloalkyl and cycloalkenyl groups may be partly or completely fluorinated or mono- or disubstituted by identical or different substituents selected from chlorine, cyano, hydroxy, $C_{1-3}$-alkoxy, $C_{1-3}$-alkylsulphanyl, $-NH_2$, $-NHR^N$, $-NR^N(C_{1-3}$-alkyl) and $C_{1-3}$-alkyl, and in cycloalkyl and cycloalkenyl groups one or two methylene groups may be replaced independently of one another by O, S, CO, SO or $SO_2$, and Z denotes oxygen, methylene, dimethylmethylene, 1,1-cyclopropylene, difluoromethylene or carbonyl;

while by the aryl groups mentioned in the definition of the above-mentioned groups are meant phenyl or naphthyl groups, which may be mono- or disubstituted independently of one another by identical or different groups L; and by the heteroaryl groups mentioned in the definition of the above-mentioned groups are meant a pyrrolyl, furanyl, thienyl, imidazolyl, pyridyl, indolyl, benzofuranyl, benzothiophenyl, quinolinyl or isoquinolinyl group, or a pyrrolyl, furanyl, thienyl, imidazolyl or pyridyl group, wherein one or two methyne groups are replaced by nitrogen atoms, or an indolyl, benzofuranyl, benzothiophenyl, quinolinyl or isoquinolinyl group, wherein one to three methyne groups are replaced by nitrogen atoms, while the above-mentioned heteroaryl groups may independently of one another be mono- or disubstituted by identical or different groups L;

while by the N-heterocycloalkyl group mentioned in the definition of the above-mentioned groups is meant a saturated carbocyclic ring which comprises an imino group in the ring, which may comprise a further imino group or an O or S atom in the ring, and unless otherwise stated, the above-mentioned alkyl groups may be straight-chain or branched, the tautomers, the stereoisomers, the mixtures thereof and the salts thereof, particularly the physiologically acceptable salts thereof.

The compounds of general formula I according to the invention and the physiologically acceptable salts thereof have valuable pharmacological properties, particularly an inhibitory effect on the sodium-dependent glucose cotransporter SGLT, particularly SGLT2. Moreover compounds according to the invention may have an inhibitory effect on the sodium-dependent glucose cotransporter SGLT1. Compared with a possible inhibitory effect on SGLT1 the compounds according to the invention preferably inhibit SGLT2 selectively.

The present invention also relates to the physiologically acceptable salts of the compounds according to the invention with inorganic or organic acids.

The invention therefore also relates to the use of the compounds according to the invention, including the physiologically acceptable salts thereof, as pharmaceutical compositions.

This invention also relates to pharmaceutical compositions, containing at least one compound according to the invention or a physiologically acceptable salt according to the invention, optionally together with one or more inert carriers and/or diluents.

This invention also relates to the use of at least one compound according to the invention or one of the physiologically acceptable salts of such a compound for preparing a pharmaceutical composition which is suitable for the treatment or prevention of diseases or conditions which can be influenced by inhibiting the sodium-dependent glucose cotransporter SGLT, particularly SGLT2.

This invention also relates to the use of at least one compound according to the invention for preparing a pharmaceutical composition which is suitable for the treatment of metabolic disorders.

This invention also relates to the use of at least one compound according to the invention for preparing a pharmaceutical composition for inhibiting the sodium-dependent glucose cotransporter SGLT, particularly SGLT2.

The invention further relates to a process for preparing a pharmaceutical composition according to the invention, characterised in that a compound according to the invention is incorporated in one or more inert carriers and/or diluents by a non-chemical method.

The present invention also relates to a process for preparing the compounds of general formula I according to the invention, characterised in that a) in order to prepare compounds of general formula I which are defined as hereinbefore and hereinafter,
a compound of general formula II

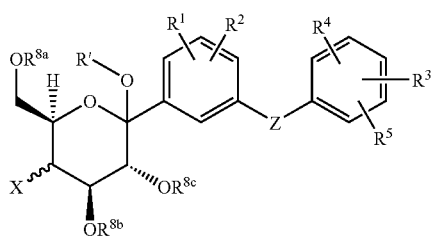

wherein
R' denotes H, $C_{1-4}$-alkyl, ($C_{1-18}$-alkyl)carbonyl, ($C_{1-18}$-alkyl)oxycarbonyl, arylcarbonyl or aryl-($C_{1-3}$-alkyl)-carbonyl, wherein the alkyl or aryl groups may be mono- or polysubstituted by halogen;
$R^{8a}$, $R^{8b}$,
$R^{8c}$ independently of one another have one of the meanings given hereinbefore and hereinafter for the groups $R^{7a}$, $R^{7b}$, $R^{7c}$, denote a benzyl group or a $R^aR^bR^cSi$ group or a ketal or acetal group, while in each case two adjacent groups $R^{8a}$, $R^{8b}$, $R^{8c}$ may form a cyclic ketal or acetal group or with two oxygen atoms of the pyranose ring may form a substituted 2,3-oxydioxane ring, particularly a 2,3-dimethyl-2,3-di($C_{1-3}$-alkoxy)-1,4-dioxane ring, and alkyl, aryl and/or benzyl groups may be mono- or polysubstituted by halogen, $C_{1-3}$-alkyl or $C_{1-3}$-alkoxy and benzyl groups may also be substituted by a di-($C_{1-3}$-alkyl)amino group; and $R^a$, $R^b$, $R^c$ independently of one another represent $C_{1-4}$-alkyl, aryl or aryl-$C_{1-3}$-alkyl, wherein the aryl or alkyl groups may be mono- or polysubstituted by halogen;
while by the aryl groups mentioned in the definition of the above-mentioned groups are meant phenyl or naphthyl groups, preferably phenyl groups;
and wherein the groups X and $R^1$ to $R^5$ and the bridge Z are defined as hereinbefore and hereinafter;
is reacted with a reducing agent in the presence of an acid, while any protecting groups present are cleaved at the same time or subsequently; or b) in order to prepare compounds of general formula I wherein $R^{7a}$, $R^{7b}$ and $R^{7c}$ denote hydrogen,
in a compound of general formula III

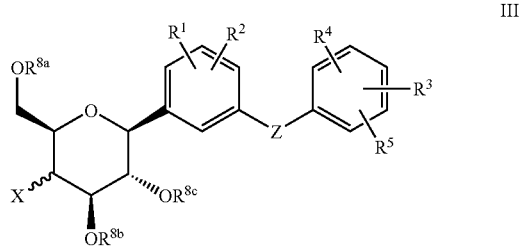

wherein X, Z, $R^{8a}$, $R^{8b}$, $R^{8c}$ and $R^1$ to $R^5$ are defined as hereinbefore and hereinafter, and at least one of the groups $R^{8a}$, $R^{8b}$ and $R^{8c}$ does not represent hydrogen,
the groups $R^{8a}$, $R^{8b}$ or $R^{8c}$ which do not represent hydrogen are removed, particularly hydrolysed; and
any protecting group used in the reactions described above under process a) or b) is cleaved and/or
if desired a compound of general formula I thus obtained is selectively derivatised at a hydroxy group or substituted and/or
if desired a compound of general formula I thus obtained is resolved into its stereoisomers and/or
if desired a compound of general formula I thus obtained is converted into the salts thereof, particularly, for pharmaceutical use, into the physiologically acceptable salts thereof.

DETAILED DESCRIPTION OF THE INVENTION

Unless otherwise stated the groups, residues and substituents, particularly $R^1$ to $R^5$, X, Z, L, $R^N$, $R^{7a}$, $R^{7b}$, $R^{7c}$ have the meanings given above and hereinafter.

If residues, substituents or groups appear more than once in a compound, they may have the same or different meanings.

The compounds according to the invention may be in the β-D-glucopyranosyl configuration (formula IA) or in the β-D-galactopyranosyl configuration (formula IB).

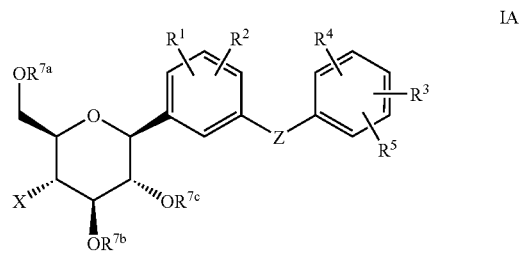

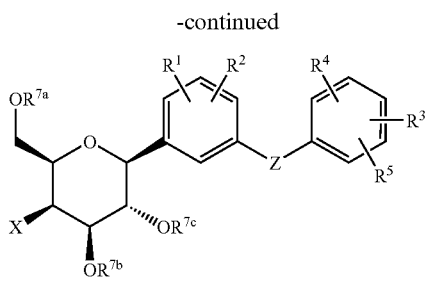

IB

With regard to inhibiting SGLT2 and preferably a higher selectivity of the inhibitory effect on SGLT2 compared with SGLT1, compounds of formula IA are preferred.

The group $R^3$ is preferably in the meta or para position to the -Z- bridge. Therefore the compounds of general formula IA according to the invention are preferably described according to the following formulae IA.1 and IA.2, particularly formula IA.2:

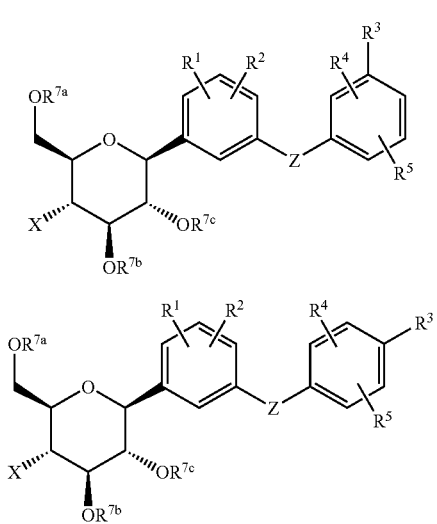

The term aryl used above and hereinafter, for example in the groups X, $R^1$ and $R^3$, preferably denotes phenyl. According to the general definition and unless otherwise stated, the aryl group, particularly the phenyl group, may be mono- or disubstituted by identical or different groups L.

The term heteroaryl used above and hereinafter, for example in the groups X, $R^1$ and $R^3$, preferably denotes pyridinyl, pyrimidinyl, pyridazinyl, pyrazinyl, triazinyl, imidazolyl, pyrazolyl, triazolyl, tetrazolyl, oxazolyl, oxadiazolyl, thiazolyl or thiadiazolyl. According to the general definition and unless otherwise stated, the heteroaryl group may be mono- or disubstituted by identical or different groups L.

Preferably $R^1$ denotes hydrogen, fluorine, chlorine, bromine, iodine, $C_{1-6}$-alkyl, $C_{2-6}$-alkynyl, $C_{2-6}$-alkenyl, $C_{3-7}$-cycloalkyl, $C_{5-7}$-cycloalkenyl, $C_{1-4}$-alkylcarbonyl, aminocarbonyl, $C_{1-4}$-alkyl-aminocarbonyl, di-($C_{1-3}$-alkyl)aminocarbonyl, $C_{1-4}$-alkoxycarbonyl, $C_{1-4}$-alkylamino, di-($C_{1-3}$-alkyl)amino, pyrrolidin-1-yl, piperidin-1-yl, morpholin-4-yl, $C_{1-4}$-alkylcarbonylamino, $C_{1-6}$-alkyloxy, $C_{3-7}$-cycloalkyloxy, $C_{5-7}$-cycloalkenyloxy, $C_{1-4}$-alkylsulphanyl, $C_{1-4}$-alkylsulphonyl, $C_{3-7}$-cycloalkylsulphanyl, $C_{3-7}$-cycloalkylsulphonyl, $C_{5-7}$-cycloalkenylsulphanyl, $C_{5-7}$-cycloalkenylsulphonyl, hydroxy and cyano, while alkyl, alkenyl, alkynyl, cycloalkyl and cycloalkenyl groups may be partly or completely fluorinated or mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be replaced by CO or $SO_2$.

If the group $R^1$ denotes a cycloalkyl or cycloalkenyl group wherein one or two methylene groups are replaced independently of one another by O, S, CO, SO or $SO_2$, preferred meanings of the group $R^1$ are selected from among tetrahydrofuranyl, tetrahydrofuranonyl, tetrahydrothienyl, tetrahydropyranyl, tetrahydropyranonyl, dioxanyl and trioxanyl.

If the group $R^1$ denotes an N-heterocycloalkyl group wherein a methylene group is substituted by CO or $SO_2$, preferred meanings of the group $R^1$ are selected from among pyrrolidinone, piperidinone, piperazinone and morpholinone.

Particularly preferably $R^1$ denotes hydrogen, fluorine, chlorine, bromine, iodine, $C_{1-6}$-alkyl, $C_{2-6}$-alkynyl, $C_{2-6}$-alkenyl, $C_{3-7}$-cycloalkyl, $C_{5-7}$-cycloalkenyl, $C_{1-6}$-alkyloxy, $C_{3-7}$-cycloalkyloxy or cyano, while in cycloalkyl and cycloalkenyl groups one or two methylene units may be replaced independently of one another by O or CO and alkyl, alkenyl and alkynyl groups may be partly or completely fluorinated.

Examples of the most particularly preferred $R^1$ are hydrogen, fluorine, chlorine, bromine, methyl, ethyl, isopropyl, trifluoromethyl, ethynyl, methoxy, cyclopentyloxy and cyano.

The group $R^3$ preferably denotes hydrogen, fluorine, chlorine, bromine, $C_{1-6}$-alkyl, $C_{2-6}$-alkynyl, $C_{2-6}$-alkenyl, $C_{3-7}$-cycloalkyl, $C_{3-7}$-cycloalkyl-methyl, $C_{5-7}$-cycloalkenyl, $C_{3-7}$-cycloalkenyl-methyl, aryl, heteroaryl, $C_{1-4}$-alkylcarbonyl, aminocarbonyl, $C_{1-4}$-alkyl-aminocarbonyl, di-($C_{1-3}$-alkyl)-aminocarbonyl, $C_{1-4}$-alkoxycarbonyl, di-($C_{1-3}$-alkyl)amino, pyrrolidin-1-yl, piperidin-1-yl, morpholin-4-yl, $C_{1-4}$-alkylcarbonylamino, $C_{1-6}$-alkoxy, $C_{3-7}$-cycloalkyloxy, $C_{5-7}$-cycloalkenyloxy, aryloxy, heteroaryloxy, $C_{1-4}$-alkylsulphanyl, $C_{1-4}$-alkylsulphonyl, $C_{3-7}$-cycloalkylsulphanyl, $C_{3-7}$-cycloalkylsulphonyl, $C_{5-7}$-cycloalkenylsulphanyl, $C_{5-7}$-cycloalkenylsulphonyl, hydroxy and cyano, while alkyl, alkenyl, alkynyl, cycloalkyl and cycloalkenyl groups may be partly or completely fluorinated or mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be replaced by CO or $SO_2$, while the terms aryl and heteroaryl are as hereinbefore defined and aryl and heteroaryl groups may independently of one another be mono- or disubstituted by identical or different groups L.

If the group $R^3$ denotes a cycloalkyl or cycloalkenyl group wherein one or two methylene groups are replaced independently of one another by O, S, CO, SO or $SO_2$, preferred definitions of the group $R^3$ are selected from among tetrahydrofuranyl, tetrahydrofuranonyl, tetrahydrothienyl, tetrahydropyranyl, tetrahydropyranonyl, dioxanyl and trioxanyl.

If the group $R^3$ denotes an N-heterocycloalkyl group wherein a methylene group is replaced by CO or $SO_2$, preferred meanings of the group $R^3$ are selected from among pyrrolidinone, piperidinone, piperazinone and morpholinone.

Particularly preferred $R^3$ are $C_{1-6}$-alkyl, $C_{2-6}$-alkynyl, $C_{1-4}$-alkyloxy, $C_{3-7}$-cycloalkyl, $C_{3-7}$-cycloalkyloxy and hydroxy, while in the cycloalkyl groups one or two methylene units may independently of one another be replaced by O or CO and alkyl groups may be partly or completely fluorinated.

Most particularly preferred groups $R^3$ are methyl, ethyl, ethynyl, isopropyl, methoxy, ethoxy, isopropyloxy, difluoromethoxy, cyclopentyloxy, tetrahydrofuran-3-yloxy and hydroxy.

The group X has one of the definitions given hereinbefore and hereinafter, while X does not represent a hydroxy group and preferably does not denote a group which is converted under physiological conditions to any significant extent into a hydroxy group. In particular, the group X is not an alkylcarbonyloxy, (het)arylcarbonyloxy, alkyloxycarbonyloxy or (het)aryloxycarbonyloxy group, where (het)aryl denotes an aryl or heteroaryl group.

The group X preferably denotes hydrogen, fluorine, chlorine, $C_{1-6}$-alkyl, $C_{2-6}$-alkynyl, $C_{2-6}$-alkenyl, $C_{3-7}$-cycloalkyl-$C_{1-3}$-alkyl, $C_{5-7}$-cycloalkenyl-$C_{1-3}$-alkyl, aryl-$C_{1-3}$-alkyl, heteroaryl-$C_{1-3}$-alkyl, $C_{1-6}$-alkoxy, $C_{2-6}$-alkenyloxy, $C_{2-6}$-alkynyloxy, $C_{3-7}$-cycloalkyloxy, $C_{5-7}$-cycloalkenyloxy, aryloxy, heteroaryloxy, $C_{3-7}$-cycloalkyl-$C_{1-3}$-alkyloxy, $C_{5-7}$-cyclo-alkenyl-$C_{1-3}$-alkyloxy, aryl-$C_{1-3}$-alkyloxy, heteroaryl-$C_{1-3}$-alkyloxy, $C_{3-7}$-cycloalkyloxy-$C_{1-3}$-alkyl, $C_{5-7}$-cycloalkenyloxy-$C_{1-3}$-alkyl, aryloxy-$C_{1-3}$-alkyl, heteroaryloxy-$C_{1-3}$-alkyl, aminocarbonyl, $C_{1-4}$-alkylaminocarbonyl, $C_{1-4}$-alkylcarbonylamino, N—($C_{1-5}$-alkyl)-N—($C_{1-4}$-alkylcarbonyl)-amino, hydroxycarbonyl, $C_{1-4}$-alkoxycarbonyl, $C_{1-6}$-alkylsulphonyl, aminocarbonyl-$C_{1-3}$-alkyl, $C_{1-4}$-alkylaminocarbonyl-$C_{1-3}$-alkyl, di-($C_{1-3}$-alkyl)aminocarbonyl-$C_{1-3}$-alkyl, $C_{1-4}$-alkoxycarbonyl-$C_{1-3}$alkyl, amino, $C_{1-5}$-alkylamino, N—($C_{1-5}$-alkyl)-N—($C_{1-3}$-alkyl)-amino, mercapto or cyano, while alkyl, alkenyl, alkynyl, cycloalkyl and cycloalkenyl groups may be partly or completely fluorinated or mono- or disubstituted by identical or different substituents selected from chlorine, cyano, hydroxy, $C_{1-3}$-alkoxy, $C_{1-3}$-alkylsulphanyl, —$NH_2$, —$NHR^N$, —$NR^N(C_{1-3}$-alkyl) and $C_{1-3}$-alkyl, and in the above-mentioned cycloalkyl and cycloalkenyl groups one or two methylene groups may be replaced independently of one another by O, S, CO, SO or $SO_2$, and the terms aryl and heteroaryl are as hereinbefore defined and aryl and heteroaryl groups may independently of one another be mono- or disubstituted by identical or different groups L.

The compounds according to the invention can be formally divided up, in accordance with the different definitions of the group X, into different embodiments:

According to a first embodiment X preferably denotes hydrogen, chlorine, cyano, $C_{1-6}$-alkyl, $C_{2-6}$-alkynyl, $C_{2-6}$-alkenyl, $C_{3-7}$-cycloalkyl-$C_{1-3}$-alkyl, $C_{5-7}$-cycloalkenyl-$C_{1-3}$-alkyl, aryl-$C_{1-3}$-alkyl, heteroaryl-$C_{1-3}$-alkyl, aminocarbonyl, $C_{1-4}$-alkylaminocarbonyl, hydroxycarbonyl, $C_{1-4}$-alkoxycarbonyl, $C_{1-6}$-alkylsulphonyl, $C_{3-7}$-cycloalkyloxy-$C_{1-3}$-alkyl, $C_{5-7}$-cycloalkenyloxy-$C_{1-3}$-alkyl, aryloxy-$C_{1-3}$-alkyl and heteroaryloxy-$C_{1-3}$-alkyl, while alkyl, alkenyl, alkynyl, cycloalkyl and cycloalkenyl groups may be partly or completely fluorinated or mono- or disubstituted by identical or different substituents selected from chlorine, cyano, hydroxy, $C_{1-3}$-alkylsulphanyl, $NHR^N$, $C_{1-3}$-alkyl-$NR^N$, $C_{1-3}$-alkoxy and $C_{1-3}$-alkyl, and methyl groups may be partly or completely fluorinated or monosubstituted by chlorine, and in the above-mentioned cycloalkyl and cycloalkenyl groups one or two methylene groups may be replaced independently of one another by O, S, CO, SO or $SO_2$, and the terms aryl and heteroaryl are as hereinbefore defined and aryl and heteroaryl groups independently of one another may be mono- or disubstituted by identical or different groups L.

If the group X denotes a cycloalkyl or cycloalkenyl group wherein one or two methylene groups are replaced independently of one another by O, S, CO, SO or $SO_2$, preferred definitions of the group X are selected from among tetrahydrofuranyl, tetrahydrofuranonyl, tetrahydrothienyl, tetrahydropyranyl, tetrahydropyranonyl, dioxanyl and trioxanyl.

Particularly preferred residues of the group X are hydrogen, chlorine, cyano, $C_{1-6}$-alkyl, $C_{2-6}$-alkynyl, $C_{2-6}$-alkenyl, $C_{1-6}$-alkylsulphonyl, hydroxycarbonyl, $C_{1-4}$-alkoxycarbonyl, aminocarbonyl and $C_{1-4}$-alkylaminocarbonyl, while alkyl groups may be mono- or polyfluorinated or monosubstituted by hydroxy or cyano.

Most particularly preferred groups X are hydrogen, chlorine, cyano, methyl, ethyl, propyl, hydroxymethyl, prop-2-enyl, prop-2-ynyl, methylsulphonyl, aminocarbonyl, methylaminocarbonyl, hydroxycarbonyl and methoxycarbonyl.

A selection of the most particularly preferred groups X comprises hydrogen, chlorine, methyl, hydroxymethyl and ethyl.

According to a second embodiment X preferably denotes $C_{1-6}$-alkoxy, $C_{2-6}$-alkenyloxy, $C_{2-6}$-alkynyloxy, $C_{3-7}$-cycloalkyloxy, $C_{5-7}$-cycloalkenyloxy, aryloxy, aryl-$C_{1-3}$-alkyloxy or heteroaryloxy, while the above-mentioned alkoxy, cycloalkyl and cycloalkenyl groups may be partly or completely fluorinated or mono- or disubstituted by identical or different substituents selected from hydroxy, $C_{1-3}$-alkoxy and $C_{1-3}$-alkyl, and in the above-mentioned cycloalkyl and cycloalkenyl groups one or two methylene groups may be replaced independently of one another by O, S, CO, SO or $SO_2$, and the terms aryl and heteroaryl are as hereinbefore defined and aryl and heteroaryl groups independently of one another may be mono- or disubstituted by identical or different groups L.

According to this embodiment preferred meanings of the group X are $C_{1-6}$-alkyloxy, $C_{2-6}$-alkenyloxy, $C_{2-6}$-alkynyloxy, $C_{3-7}$-cycloalkyloxy, aryl-$C_{1-3}$-alkyloxy and aryloxy, while by aryl is meant a phenyl or naphthyl group, particularly phenyl, which may be mono- or disubstituted by identical or different substituents L.

Particularly preferred meanings of the group X are methoxy and ethoxy.

According to a third embodiment X preferably denotes mercapto, $C_{1-5}$-alkylsulphanyl, $C_{2-5}$-alkenylsulphanyl, $C_{2-5}$-alkynylsulphanyl, $C_{3-7}$-cycloalkylsulphanyl, $C_{5-7}$-cycloalkenylsulphanyl, arylsulphanyl or heteroarylsulphanyl, while the above-mentioned alkoxy, cycloalkyl and cycloalkenyl groups may be partly or completely fluorinated or mono- or disubstituted by identical or different substituents selected from hydroxy, $C_{1-3}$-alkoxy and $C_{1-3}$-alkyl, and in the above-mentioned cycloalkyl and cycloalkenyl groups one or two methylene groups may be replaced independently of one another by O, S, CO, SO or $SO_2$, and the terms aryl and heteroaryl are as hereinbefore defined and aryl and heteroaryl groups independently of one another may be mono- or disubstituted by identical or different groups L.

According to this embodiment preferred meanings of the group X are mercapto, $C_{1-5}$-alkylsulphanyl, $C_{2-5}$-alkenylsulphanyl, $C_{2-5}$-alkynylsulphanyl, $C_{3-7}$-cycloalkylsulphanyl and arylsulphanyl, while by aryl is meant a phenyl or naphthyl group, particularly phenyl, which may be mono- or disubstituted by identical or different substituents L.

Particularly preferred meanings of the group X are mercapto, methylsulphanyl and ethylsulphanyl.

According to a fourth embodiment X preferably denotes amino, $C_{1-5}$-alkylamino, N—($C_{1-5}$-alkyl)-N—($C_{1-3}$-alkyl)-amino, $C_{1-4}$-alkylcarbonylamino, N—($C_{1-5}$-alkyl)-N—($C_{1-4}$-alkylcarbonyl)-amino, $C_{2-5}$-alkenylamino, $C_{2-5}$-alkynylamino, $C_{3-7}$-cycloalkylamino, $C_{5-7}$-cycloalkenylamino, arylamino or heteroarylamino, while the above-mentioned alkoxy, cycloalkyl and cycloalkenyl groups may be partly or completely fluorinated or mono- or disubstituted by identical or different substituents selected from hydroxy, $C_{1-3}$-alkoxy and $C_{1-3}$-alkyl, and in the above-mentioned cycloalkyl and cycloalkenyl groups one or two methylene groups may be replaced independently of one another by O, S, CO, SO or $SO_2$, and the terms aryl and heteroaryl are as hereinbefore defined and aryl and heteroaryl groups may independently of one another be mono- or disubstituted by identical or different groups L.

According to this embodiment preferred meanings of the group X are amino, $C_{1-5}$-alkylamino, N—($C_{1-5}$-alkyl)-N—($C_{1-3}$-alkyl)-amino, $C_{1-4}$-alkylcarbonylamino, N—($C_{1-5}$-alkyl)-N—($C_{1-4}$-alkylcarbonyl)-amino and arylamino, while by aryl is meant a phenyl or naphthyl group, particularly phenyl, which may be mono- or disubstituted by identical or different substituents L.

Particularly preferred meanings of the group X are amino, methylamino, dimethylamino and methylcarbonylamino.

According to a fifth embodiment X denotes fluorine.

According to a sixth embodiment X preferably denotes bromine, iodine, $C_{1-6}$alkyl-sulphonyloxy, arylsulphonyloxy or aryl-$C_{1-3}$-alkyl-sulphonyloxy, while the above-mentioned alkyl groups may be partly or completely fluorinated or mono- or dichlorinated and the above-mentioned aryl groups may be mono- or disubstituted by identical or different groups L. L is preferably selected from among fluorine, chlorine, bromine, iodine, $C_{1-3}$-alkyl, difluoromethyl, trifluoromethyl and cyano.

The compounds according to this sixth embodiment are particularly suitable, beyond their pharmaceutical activity as described, as intermediate products in the synthesis of compounds with an SGLT, preferably SGLT2 inhibiting activity, particularly in the synthesis of other compounds according to the invention. When used as intermediate products for synthesising compounds of general formula I the groups X described here may also be linked to the pyranose ring in the inverted stereochemical position compared with the desired product.

Particularly preferred groups X according to this sixth embodiment are bromine, iodine, $C_{1-4}$-alkylsulphonyloxy, phenylsulphonyloxy or phenylmethylsulphonyloxy, while the above-mentioned alkyl groups may e partly or completely fluorinated and the above-mentioned phenyl groups may be mono- or disubstituted by identical or different groups L. L is preferably selected from among fluorine, chlorine, bromine and methyl.

Most particularly preferred is X with the meaning of trifluoromethylsulphonyloxy or iodine.

Preferred compounds according to the invention are those which have a group X according to the first, second, third, fourth and fifth embodiment described above, and particularly have a group X according to the definitions specified therein as being preferred. Most particularly preferred are the first, second, fourth and fifth embodiment.

If there are cycloalkyl or cycloalkenyl rings in the residues or groups X, $R^1$ or $R^3$ wherein two methylene groups are replaced by O or S or by CO, SO or $SO_2$, these methylene groups are preferably not directly connected to one another. If however two methylene groups are replaced by O and CO, these may be directly connected to one another, so as to form a carboxy group. If X, $R^1$ or $R^3$ is a cycloalkyl or cycloalkenyl group with one or two methylene groups which are replaced according to the invention, the relevant group X, $R^1$ or $R^3$ preferably denotes a cycloalkyl or cycloalkenyl group wherein a methylene group is substituted by O, S, CO, SO or $SO_2$ or an ethylene group is substituted by —O—CO— or —CO—O—.

The meanings of some other groups and substituents will now be given, which are to be regarded as preferred according to general formula I, particularly formulae IA and IB and also according to the embodiments described hereinbefore:

Preferred meanings of the group $R^2$ are hydrogen, fluorine, chlorine, bromine, methyl, hydroxy, methoxy, ethoxy, trifluoromethoxy, cyano, nitro and methyl substituted by 1 to 3 fluorine atoms.

Particularly preferred meanings of the group $R^2$ are hydrogen, fluorine, hydroxy, methoxy, ethoxy and methyl, particularly hydrogen and methyl.

If $R^1$ and $R^2$ are bound to two adjacent C atoms of the phenyl ring, $R^1$ and $R^2$ may be joined together such that $R^1$ and $R^2$ together preferably form a $C_{3-4}$-alkylene bridge, wherein one or two methylene units independently of one another may be replaced by O, $NR^N$ or CO or a butadienylene bridge, wherein a methyne group may be replaced by a nitrogen atom, while the bridging groups mentioned may be partly or completely fluorinated or mono- or disubstituted by identical or different substituents selected from chlorine, hydroxy, $C_{1-3}$-alkoxy and $C_{1-3}$-alkyl. Preferably the linked groups $R^1$ and $R^2$ together with the phenyl ring by which they are joined form a bicyclic ring system selected from indan, dihydroindole, dihydrobenzofuran, tetrahydroquinoline, dihydroquinolinone, tetrahydroisoquinoline, dihydroisoquinolinone, tetrahydronaphthalene, naphthalene, quinoline or isoquinoline.

Preferred meanings of the group $R^4$ are hydrogen and fluorine, particularly hydrogen.

If $R^3$ and $R^4$ are bound to two immediately adjacent C atoms of the phenyl ring, $R^3$ and $R^4$ may be joined together such that $R^3$ and $R^4$ together preferably form a $C_{3-4}$-alkylene bridge, wherein one or two methylene units independently of one another may be replaced by O, $NR^N$ or CO or a butadienylene bridge, wherein a methyne group may be replaced by a nitrogen atom, while the bridging groups mentioned may be partly or completely fluorinated or mono- or disubstituted by identical or different substituents selected from chlorine, hydroxy, $C_{1-3}$-alkoxy and $C_{1-3}$-alkyl. Preferably the linked groups $R^3$ and $R^4$ together with the phenyl ring by which they are joined form a bicyclic ring system selected from indan, dihydroindole, dihydrobenzofuran, tetrahydroquinoline, dihydroquinolinone, tetrahydroisoquinoline, dihydroisoquinolinone, tetrahydronaphthalene, naphthalene, quinoline or isoquinoline.

Preferred meanings of the group $R^5$ are hydrogen and fluorine, particularly hydrogen.

Preferred meanings of the group Z are oxygen and methylene, particularly methylene.

The substituents $R^{7a}$, $R^{7b}$, $R^{7c}$ independently of one another preferably represent hydrogen, ($C_{1-8}$-alkyl)oxycarbonyl, ($C_{1-18}$-alkyl)carbonyl, benzoyl, particularly hydrogen or ($C_{1-6}$-alkyl)oxycarbonyl, ($C_{1-8}$-alkyl)carbonyl, particularly preferably hydrogen, methoxycarbonyl, ethoxycarbonyl, methylcarbonyl or ethylcarbonyl. Most particularly preferably $R^{7a}$, $R^{7b}$ and $R^{7c}$ denote hydrogen.

The compounds of formula I wherein $R^{7a}$, $R^{7b}$ and $R^{7c}$ have a meaning according to the invention other than hydrogen, for example $C_{1-8}$-alkylcarbonyl, are preferably suitable as intermediate products in the synthesis of compounds of formula I wherein $R^{7a}$, $R^{7b}$ and $R^{7c}$ represent hydrogen.

The substituents L are preferably selected independently of one another from among fluorine, chlorine, bromine, $C_{1-3}$-alkyl, difluoromethyl, trifluoromethyl, $C_{1-3}$-alkoxy, difluoromethoxy, trifluoromethoxy and cyano, particularly preferably from among fluorine, chlorine, methyl, trifluoromethyl, methoxy and difluoromethoxy. If the substituent L is linked to an N atom, preferred meanings L are selected from $C_{1-3}$-alkyl, difluoromethyl and trifluoromethyl.

Particularly preferred compounds of general formula IA are selected from among formulae IA.2a to IA.2d, particularly formula IA.2c:

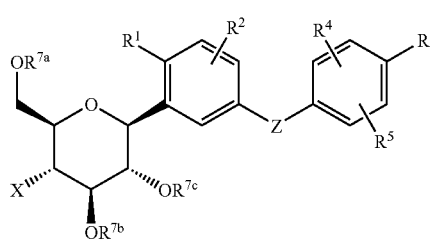

IA.2a

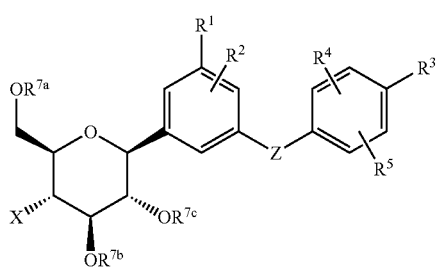

IA.2b

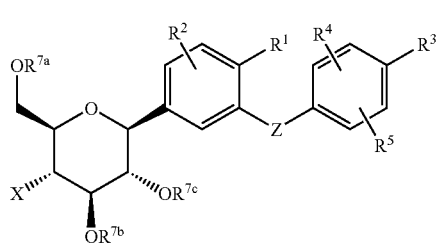

IA.2c

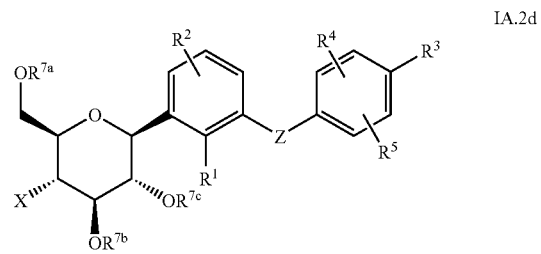

IA.2d wherein $R^1$ to $R^5$, X, Z, $R^{7a}$, $R^{7b}$, $R^{7c}$ are as hereinbefore defined.

Most particularly preferred are those compounds of formula I, particularly of formula IA or IB and, with regard to formula IA, particularly of formulae IA.2a, IA.2b, IA.2 c and IA.2d, particularly of formula IA.2c, wherein the groups $R^1$ to $R^5$, X, Z, $R^{7a}$, $R^{7b}$, $R^{7c}$ have the meanings given hereinbefore as being preferred, particularly wherein $R^1$ denotes hydrogen, fluorine, chlorine, bromine, $C_{1-6}$-alkyl, $C_{2-6}$-alkynyl, $C_{2-6}$-alkenyl, $C_{3-7}$-cycloalkyl, $C_{5-7}$-cycloalkenyl, $C_{1-6}$-alkyloxy, $C_{3-7}$-cycloalkyloxy or cyano, while in cycloalkyl and cycloalkenyl groups one or two methylene units may be replaced independently of one another by O or CO and alkyl, alkenyl and alkynyl groups may be partly or completely fluorinated, particularly preferably denotes hydrogen, fluorine, chlorine, bromine, methyl, ethyl, isopropyl, trifluoromethyl, ethynyl, methoxy, cyclopentyloxy or cyano, and $R^3$ denotes hydrogen, $C_{1-6}$-alkyl, $C_{2-6}$-alkynyl, $C_{1-4}$-alkyloxy, $C_{3-7}$-cycloalkyl, $C_{3-7}$-cycloalkyloxy or hydroxy, while in the cycloalkyl groups one or two methylene units may be replaced independently of one another by O or CO and alkyl groups may be partly or completely fluorinated; particularly preferably denotes methyl, ethyl, ethynyl, isopropyl, methoxy, ethoxy, isopropyloxy, difluoromethoxy, cyclopentyloxy, tetrahydro-furan-3-yloxy or hydroxy, and X according to a first embodiment denotes hydrogen, chlorine, cyano, $C_{1-6}$-alkyl, $C_{2-6}$-alkynyl, $C_{2-6}$-alkenyl, $C_{1-4}$-alkylcarbonyl, hydroxycarbonyl, $C_{1-4}$-alkoxy-carbonyl, aminocarbonyl, $C_{1-4}$-alkylaminocarbonyl or $C_{1-6}$-alkylsulphonyl, while alkyl groups may be mono- or polyfluorinated or monosubstituted by hydroxy or cyano; particularly preferably denotes hydrogen, chlorine, cyano, methyl, ethyl, hydroxymethyl, prop-2-enyl, prop-2-ynyl, methylsulphonyl, aminocarbonyl, methylaminocarbonyl, hydroxycarbonyl or methoxycarbonyl; or according to a second embodiment denotes $C_{1-5}$-alkyloxy, $C_{2-5}$-alkenyloxy, $C_{2-5}$-alkynyloxy, $C_{3-7}$-cycloalkyloxy, aryl-$C_{1-3}$-alkyloxy or aryloxy, while by aryl is meant a phenyl or naphthyl group, particularly phenyl, which may be mono- or disubstituted by identical or different substituents L; particularly preferably denotes ethoxy or methoxy, or according to a third embodiment denotes mercapto, $C_{1-5}$-alkylsulphanyl, $C_{2-5}$-alkenylsulphanyl, $C_{2-5}$-alkynylsulphanyl, $C_{3-7}$-cycloalkylsulphanyl or arylsulphanyl, while by aryl is meant a phenyl or naphthyl group, particularly phenyl, which may be mono- or disubstituted by identical or different substituents L; particularly preferably denotes mercapto, ethylsulphanyl or methylsulphanyl, or according to a fourth embodiment denotes amino, $C_{1-5}$-alkylamino, $N-(C_{1-5}$-alkyl)-$N-(C_{1-3}$-alkyl)-amino, $C_{1-4}$-alkylcarbonylamino, $N-(C_{1-5}$-alkyl)-$N-(C_{1-4}$-alkylcarbonyl)-amino or arylamino, while by aryl is meant a phenyl or naphthyl group, particularly phenyl, which may be mono- or disubstituted by identical or different substituents L; particularly preferably denotes amino, methylamino, dimethylamino or methylcarbonylamino, or according to a fifth embodiment denotes fluorine; and $R^2$ denotes hydrogen, fluorine, chlorine, bromine, methyl, hydroxy, methoxy, ethoxy, trifluoromethoxy, cyano, nitro or methyl substituted by 1 to 3 fluorine atoms, particularly preferably denotes hydrogen, fluorine, hydroxy, methoxy, ethoxy or methyl, particularly hydrogen or methyl, and $R^4$ denotes hydrogen or fluorine, particularly hydrogen, and $R^5$ denotes hydrogen or fluorine, particularly hydrogen, and Z denotes oxygen or methylene, particularly methylene, and $R^{7a}$, $R^{7b}$, $R^{7c}$ independently of one another denote hydrogen, $(C_{1-8}$-alkyl)oxycarbonyl, $(C_{1-18}$-alkyl)carbonyl or benzoyl, particularly hydrogen or $(C_{1-6}$-alkyl)oxycarbonyl, $(C_{1-8}$-alkyl)carbonyl, particularly preferably hydrogen, methoxycarbonyl, ethoxycarbonyl, methylcarbonyl or ethylcarbonyl, most particularly preferably hydrogen, and L independently of one another represent fluorine, chlorine, bromine, $C_{1-3}$-alkyl, difluoromethyl, trifluoromethyl, $C_{1-3}$-alkoxy, difluoromethoxy, trifluoromethoxy and cyano and if the substituent L is linked to an N atom denotes $C_{1-3}$-alkyl, difluoromethyl or trifluoromethyl;

including the tautomers, the stereoisomers, the mixtures thereof and the salts thereof, particularly the physiologically acceptable salts thereof.

According to a variant of the above-mentioned embodiments other preferred compounds are those wherein the phenyl group which carries the substituent $R^3$ has at least one other substituent $R^4$ and/or $R^5$ which is different from hydrogen. According to this variant other preferred compounds are those which have a substituent $R^4$ representing fluorine.

The phenyl group which carries the substituent $R^3$ is preferably at most difluorinated.

Particularly preferred compounds of general formula I are selected from among:
(a) 1-chloro-2-(4-methoxy-benzyl)-4-(4-O-methyl-β-D-glucopyranos-1-yl)-benzene,
(b) 1-chloro-2-(4-methoxy-benzyl)-4-(4-desoxy-β-D-glucopyranos-1-yl)-benzene,
(c) 1-chloro-2-(4-methoxy-benzyl)-4-(4-O-ethyl-β-D-glucopyranos-1-yl)-benzene,
(d) 1-chloro-2-(4-methoxy-benzyl)-4-(4-desoxy-4-fluoro-β-D-glucopyranos-1-yl)-benzene,
(e) 1-chloro-2-(4-methoxy-benzyl)-4-(4-desoxy-4-fluoro-β-D-galactopyranos-1-yl)-benzene, including the tautomers, the stereoisomers and the mixtures thereof.

Some terms used above and hereinafter to describe the compounds according to the invention will now be defined more closely.

The term halogen denotes an atom selected from the group consisting of F, Cl, Br and I, particularly F, Cl and Br.

The phrases "may be partly or completely fluorinated" and "may be mono- or polyfluorinated" which are used interchangeably indicate that the group thus designated is not fluorinated or comprises one or more fluorine substituents, and this also includes total fluorination of the group indicated.

The term $C_{1-n}$-alkyl, wherein n may have a value of 1 to 18, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term methylene denotes a —$CH_2$ group and the term methyne denotes a CH group.

The term "butadienylene" denotes the group

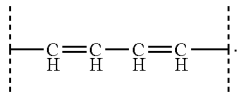

The term $C_{2-n}$-alkynyl, wherein n has a value of 3 to 6, denotes a branched or unbranched hydrocarbon group with 2 to n C atoms and a C≡C triple bond. Examples of such groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 4-methyl-2-pentynyl etc.

The term $C_{1-n}$-alkoxy or $C_{1-n}$-alkyloxy denotes a $C_{1-n}$-alkyl-O group, wherein $C_{1-n}$-alkyl is as hereinbefore defined. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy etc.

The term $C_{1-n}$-alkylcarbonyl denotes a $C_{1-n}$-alkyl-C(═O) group, wherein $C_{1-n}$-alkyl is as hereinbefore defined. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neo-pentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, decalinyl, bicyclo[3.2.1.]octyl, spiro[4.5]decyl, norpinyl, norbonyl, norcaryl, adamantyl, etc. Preferably the term $C_{3-7}$-cycloalkyl includes saturated monocyclic groups.

The term $C_{3-n}$-cycloalkyloxy denotes a $C_{3-n}$-cycloalkyl-O group, wherein $C_{3-n}$-cycloalkyl is as hereinbefore defined. Examples of such groups include cyclopropyloxy, cyclobutyloxy, cyclopentyloxy, cyclohexyloxy, cycloheptyloxy, etc.

The term $C_{5-n}$-cycloalkenyl denotes a $C_{5-n}$-cycloalkyl group which is as hereinbefore defined and additionally has at least one unsaturated C═C-double bond.

The term $C_{3-n}$-cycloalkylcarbonyl denotes a $C_{3-n}$-cycloalkyl-C(═O) group, wherein $C_{3-n}$-cycloalkyl is as hereinbefore defined.

The term tri-($C_{1-4}$-alkyl)silyl encompasses silyl groups which have identical or two or three different alkyl groups.

The term di-($C_{1-3}$-alkyl)amino encompasses amino groups which have identical or two different alkyl groups.

The term N-heterocycloalkyl denotes a saturated carbocyclic ring which comprises an imino group in the ring, and which may additionally have another imino group or an O or S atom in the ring. Examples of such N-heterocycloalkyl groups are pyrrolidine, piperidine, piperazine and morpholine.

If alkyl residues occurring in groups, for example in X, $R^1$ or $R^3$, may be substituted, e.g. fluorinated, this encompasses not only alkyl residues in the groups which represent alkyl directly but also in other definitions which include alkyl groups, such as for example alkoxy, alkylcarbonyl, alkoxyalkyl, etc. Thus, for example X, $R^1$ and $R^3$ representing alkoxy, wherein the alkyl groups may be partly or totally fluorinated, also include difluoromethoxy and trifluoromethoxy.

The style used above and hereinafter, in which a bond of a substituent in a phenyl group is shown towards the centre of the phenyl ring, denotes, unless otherwise stated, that this substituent may be bound to any free position of the phenyl group bearing an H atom.

The compounds according to the invention may be obtained using methods of synthesis known in principle. Preferably the compounds are obtained by the following methods according to the invention which are described in more detail hereinafter.

The following descriptions of preferred methods of synthesis relate to end products in a β-D-glucopyranosyl configuration, which is described by formula IA. The synthesis of the corresponding compounds in the β-D-galactopyranosyl configuration, described by formula IB, will be evident to the skilled man by analogy, and for this reason no further explanations and synthesis diagrams are provided, in the interests of clarity.

The tetrahydropyran derivatives of formula IIA according to the invention may be synthesised from D-gluconolactone or a derivative thereof by addition of the desired aryl group in the form of an organometallic compound (Diagram 1).

The reaction according to Diagram 1 is preferably carried out starting from a halogen-benzylbenzene compound of general formula IV, wherein Hal denotes chlorine, bromine or iodine. Starting from the haloaromatic compound IV the corresponding organometallic compound (V) may be prepared either by a so-called halogen-metal exchange or by insertion of the metal into the carbon-halogen bond. The halogen-metal exchange with bromine- or iodine-substituted aromatic groups may for example be carried out with an organolithium compound such as e.g. n-, sec- or tert-butyllithium and thereby yields the corresponding lithiated aromatic group. The analogous magnesium compound may also be generated by a halogen-metal exchange with a suitable Grignard compound such as e.g. isopropylmagnesium bromide or diisopropylmagnesium. The reactions are preferably carried out between 0 and –100° C., particularly preferably between –30 and –80° C., in an inert solvent or mixtures thereof, such as for example diethyl ether, tetrahydrofuran, toluene, hexane or methylene chloride. The magnesium or lithium compounds thus obtained may optionally be transmetallised with metal salts such as e.g. cerium trichloride, to form other organometallic compounds (V) suitable for addition. Alternatively the organometallic compound (V) may also be prepared by inserting a metal into the carbon-halogen bond of the haloaromatic compound IV. Metals suitable for this include e.g. lithium or magnesium. The addition of the organometallic compound V to the, gluconolactone or derivatives thereof of formula VI is preferably carried out at temperatures between 0 and –100° C., particularly preferably at –30 to –80° C., in an inert solvent or mixtures thereof, to obtain the compound of formula IIA. Suitable solvents include e.g. diethyl ether, toluene, methylene chloride, hexane, tetrahydrofuran or mixtures thereof. The reactions may be carried out without any other adjuvants or in the case of non-reactive coupling partners in the presence of Lewis acids such as e.g. $BF_3*OEt_2$ or $Me_3SiCl$ (see M. Schlosser, Organometallics in Synthesis, John Wiley & Sons, Chichester/New York/Brisbane/Toronto/Singapore, 1994). Preferred definitions of the groups $R^{8a}$, $R^{8b}$ and $R^{8c}$ are benzyl, substituted benzyl, trialkylsilyl, particu-

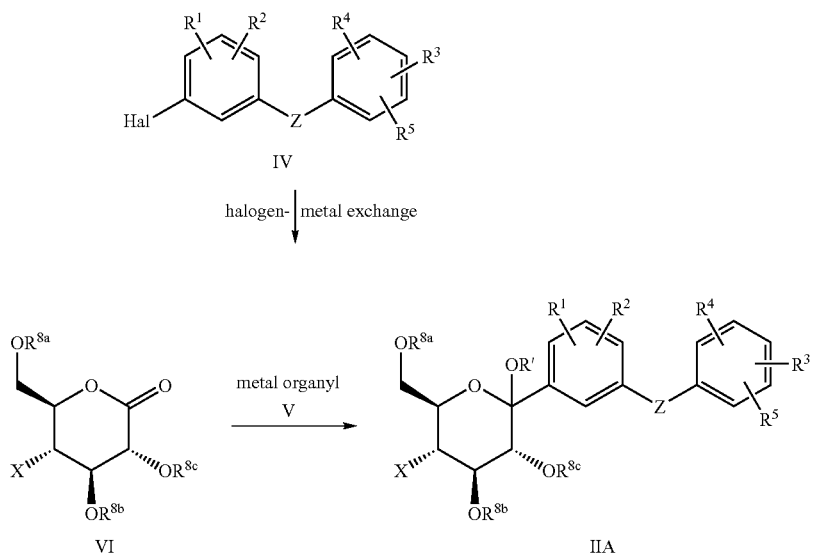

Diagram 1: Addition of an organometallic compound to a pyranone larly preferably trimethylsilyl, triisopropylsilyl, 4-methoxybenzyl and benzyl. When two adjacent groups selected from among $R^{8a}$, $R^{8b}$ and $R^{8c}$ are linked together, these two groups are preferably part of a benzylideneacetal, 4-methoxybenzylideneacetal, isopropylacetal or represent a 2,3-dimethoxybutylene group which is linked to the adjacent oxygen atoms of the pyranose ring via the 2 and 3 position of the butane. The group R' preferably denotes hydrogen or $C_{1-4}$-alkyl, particularly preferably hydrogen, methyl or ethyl. The group R' is introduced after the addition of the organometallic compound V or a derivative thereof to the gluconolactone VI. For this, the reaction solution is treated with an alcohol such as e.g. methanol or ethanol or water in the presence of an acid such as e.g. methanesulphonic acid, toluenesulphonic acid, sulphuric acid or hydrochloric acid.

The synthesis of haloaromatics of formula IV and pyranose derivatives of formula VI may be carried out using standard organic chemistry transformations or at least methods in organic chemistry which are known from the specialist literature (see inter alia J. March, Advanced Organic Reactions, Reactions, Mechanisms, and Structure, 4th Edition, John Wiley & Sons, Chichester/New York/Brisbane/Toronto/Singapore, 1992 and literature cited therein).

For synthesising the glucose derivatives it is suitable to use, apart from glucose derivatives themselves, e.g. galactose derivatives which are substituted in the 4 position by exchangeable groups $X_{AG}$ (Diagram 2). The new group X is preferably introduced by an $S_N2$ or $S_N2$-like reaction. The exchange may be carried out both on a suitable galactose derivative and also on the structure as a whole with aryl group (which is also known as aglycon). $X_{AG}$ in these reactions denotes a leaving group such as e.g. trifluoromethylsulphonyl, tosyl, mesyl, iodine or bromine and is exchanged for a C, N, O or S nucleophile, which is preferably introduced as an anion, with an inversion of the stereochemistry. However, the leaving group may also be formed in situ in the presence of the nucleophile, such as e.g. in Mitsunobu reactions. In addition to nucleophilic substitutions. It is also possible to use radical substitutions, e.g. in order to introduce a hydrogen (e.g. Barton-McCombie reaction), or also transition metal-catalysed substitutions, such as e.g. with palladium or nickel catalysts.

Diagram 2: Introduction of the group X starting from galactose derivatives

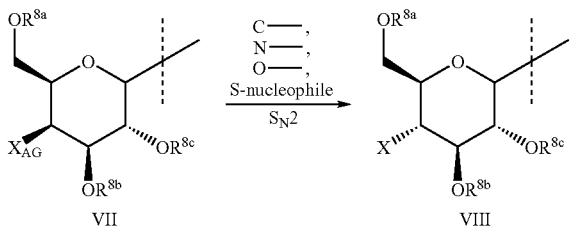

In order to prepare compounds of general formula IA, in process a) according to the invention a compound of general formula IIA

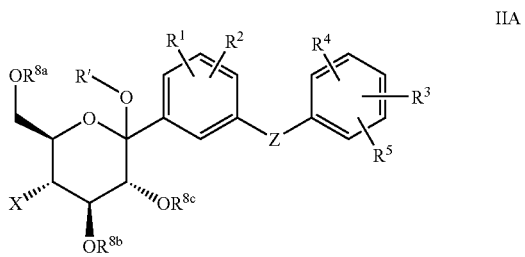

wherein X, Z and R', $R^1$ to $R^5$ are as hereinbefore defined and $R^{8a}$, $R^{8b}$ and $R^{8c}$ are as hereinbefore defined and represent for example independently of one another acetyl, pivaloyl, benzoyl, tert-butoxycarbonyl, benzyloxycarbonyl, trialkylsilyl, benzyl or substituted benzyl, Is reacted with a reducing agent in the presence of an acid.

Suitable reducing agents for the reaction include for example silanes, such as triethyl, tripropyl, triisopropyl or diphenylsilane, sodium borohydride, sodium cyanoborohydride, zinc borohydride, borane, lithium aluminium hydride, diisobutylaluminium hydride or samarium iodide. The reductions are preferably carried out in the presence of a suitable acid, such as e.g. hydrochloric acid, toluenesulphonic acid, trifluoroacetic acid, acetic acid, boron trifluoride etherate, trimethylsilyl triflate, titanium tetrachloride, tin tetrachloride, scandium triflate or zinc iodide. Depending on the reducing agent and the acid the reaction may be carried out in a solvent, such as for example methylene chloride, chloroform, acetonitrile, toluene, hexane, diethyl ether, tetrahydrofuran, dioxane, ethanol, water or mixtures thereof at temperatures between −60° C. and 120° C. A particularly suitable combination of reagents consists for example of triethylsilane and boron trifluoride etherate, which is expediently used in acetonitrile or dichloromethane at temperatures of −60° C. to 60° C. Moreover, hydrogen may be used in the presence of a transition metal catalyst, such as e.g. palladium on charcoal or Raney nickel, in solvents such as tetrahydrofuran, ethyl acetate, methanol, ethanol, water or acetic acid, for the transformation shown.

Alternatively, in order to prepare compounds of general formula IA by process b) according to the invention, in a compound of general formula IIIA

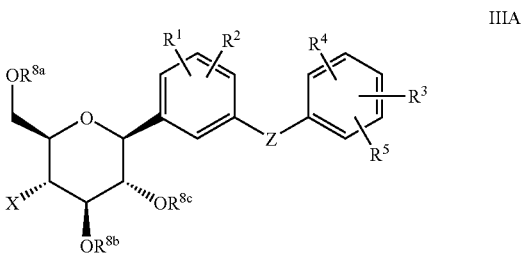

wherein X, Z and $R^1$ to $R^5$ are as hereinbefore defined and $R^{8a}$ to $R^{8c}$ denote one of the protective groups defined hereinbefore, such as e.g. an acyl, arylmethyl, acetal, ketal or silyl group, the protective groups are cleaved.

Any acyl, acetal or ketal protecting group used is cleaved, for example, hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or, in the case of acyl groups, in the presence of an alkali metal base such as lithium hydroxide, sodium hydroxide or potassium hydroxide, at temperatures between 0 and 120° C., preferably at temperatures between 10 and 100° C. A trifluoroacetyl group is preferably cleaved by treatment with an acid such as hydrochloric acid, optionally in the presence of a solvent such as acetic acid, at temperatures between 50 and 120° C. or by treatment with sodium hydroxide solution, optionally in the presence of a solvent such as tetrahydrofuran or methanol, at temperatures between 0 and 50° C.

A trimethylsilyl group is cleaved for example in water, an aqueous solvent mixture or a lower alcohol such as methanol or ethanol in the presence of a base such as lithium hydroxide, sodium hydroxide, potassium carbonate or sodium methoxide. In aqueous or alcoholic solvents, acids such as e.g. hydrochloric acid, trifluoroacetic acid or acetic acid are also suitable. Fluoride reagents, such as e.g. tetrabutylammonium fluoride, are also suitable for cleaving in organic solvents, such as for example diethyl ether, tetrahydrofuran or dichloromethane.

A benzyl, methoxybenzyl or benzyloxycarbonyl group is advantageously cleaved hydrogenolytically, e.g. with hydrogen in the presence of a catalyst such as palladium/charcoal, in a suitable solvent such as methanol, ethanol, ethyl acetate or glacial acetic acid, optionally with the addition of an acid such as hydrochloric acid, at temperatures between 0 and 100° C., but preferably at ambient temperatures between 20 and 60° C., and under a hydrogen pressure of 1 to 7 bar, but preferably from 3 to 5 bar. However, a 2,4-dimethoxybenzyl group is preferably cleaved in trifluoroacetic acid in the presence of anisole.

A tert-butyl or tert-butyloxycarbonyl group is preferably cleaved by treatment with an acid such as trifluoroacetic acid or hydrochloric acid or by treatment with iodotrimethylsilane, optionally using a solvent such as methylene chloride, dioxane, methanol or diethyl ether.

In the reactions described hereinbefore, any reactive groups present such as ethynyl, hydroxy, amino, alkylamino or imino groups may be protected during the reaction by conventional protecting groups which are cleaved again after the reaction, e.g. as described above.

For example, a protecting group for an ethynyl group may be a trimethylsilyl or triisopropylsilyl group.

For example, a protecting group for a hydroxy group may be a trimethylsilyl, acetyl, trityl, benzyl or tetrahydropyranyl group.

Examples of protecting groups for an amino, alkylamino or imino group include the formyl, acetyl, trifluoroacetyl, ethoxycarbonyl, tert-butoxycarbonyl, benzyloxycarbonyl, benzyl, methoxybenzyl or 2,4-dimethoxybenzyl group.

Furthermore, the compounds of general formula I thus obtained may be selectively derivatised at a hydroxy group or the hydroxy group itself may be substituted.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-O-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)-or (−)-menthyloxycarbonyl.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, the compounds obtained may be converted into mixtures, for example 1:1 or 1:2 mixtures with amino acids, particularly with alpha-amino acids such as proline or phenylalanine, which may have particularly favourable properties such as a high crystallinity.

The compounds of general formulae II and III used as starting materials are partly known from the literature or may be obtained by methods known from the literature and also analogously to the methods described in the Examples, optionally with the additional inclusion of protecting groups.

The compounds according to the invention may advantageously also be obtained by the methods described in the following Examples, which may also be combined with methods known to the skilled man from the literature, for example, particularly the methods described in WO 98/31697, WO 01/27128, WO 02/083066, WO 03/099836, WO 2004/063209 and WO 2004/052902.

As already mentioned hereinbefore, the compounds of general formula I according to the invention and the physiologically acceptable salts thereof have valuable pharmacological properties, particularly an inhibitory effect on the sodium-dependent glucose cotransporter SGLT. With regard to the inhibition of SGLT2 and preferably a higher selectivity of the inhibitory effect on SGLT2 compared with SGLT1, compounds of formula IA are preferred.

The biological properties of the new compounds may be investigated as follows:

The ability of the substances to inhibit the SGLT-2 activity may be demonstrated in a test set-up in which a CHO-K1 cell line (ATCC No. CCL 61) or alternatively an HEK293 cell line (ATCC No. CRL-1573), which is stably transfected with an expression vector pZeoSV (Invitrogen, EMBL accession number L36849), which contains the cDNA for the coding sequence of the human sodium glucose cotransporter 2 (Genbank Acc. No.NM_003041) (CHO-hSGLT2 or HEK-hS-GLT2). These cell lines transport $^{14}$C-labelled alpha-methyl-glucopyranoside ($^{14}$C-AMG, Amersham) into the interior of the cell in sodium-dependent manner.

The SGLT-2 assay is carried out as follows:

CHO-hSGLT2 cells are cultivated in Ham's F12 Medium (BioWhittaker) with 10% foetal calf serum and 250 µg/ml zeocin (Invitrogen), and HEK293-hSGLT2 cells are cultivated in DMEM medium with 10% foetal calf serum and 250 µg/ml zeocin (Invitrogen).

The cells are detached from the culture flasks by washing twice with PBS and subsequently treating with trypsin/EDTA. After the addition of cell culture medium the cells are centrifuged, resuspended in culture medium and counted in a Casy cell counter. Then 40,000 cells per well are seeded into a white, 96-well plate coated with poly-D-lysine and incubated overnight at 37° C., 5% $CO_2$. The cells are washed twice with 250 µl of assay buffer (Hanks Balanced Salt Solution, 137 mM NaCl, 5.4 mM KCl, 2.8 mM $CaCl_2$, 1.2 mM $MgSO_4$ and 10 mM HEPES (pH7.4), 50 µg/ml of gentamycin). 250 µl of assay buffer and 5 µl of test compound are then added to each well and the plate is incubated for a further 15 minutes in the incubator. 5 µl of 10% DMSO are used as the negative control. The reaction is started by adding 5 µl of $^{14}$C-AMG (0.05 µCi) to each well. After 2 hours' incubation at 37° C., 5% $CO_2$, the cells are washed again with 250 µl of PBS (20° C.) and then lysed by the addition of 25 µl of 0.1 N NaOH (5 min. at 37° C.). 200 µl of MicroScint20 (Packard) are added to each well and incubation is continued for a further 20 min at 37° C. After this incubation the radioactivity of the $^{14}$C-AMG absorbed is measured in a Topcount (Packard) using a $^{14}$C scintillation program.

To determine the selectivity with respect to human SGLT1 an analogous test is set up in which the cDNA for hSGLT1 (Genbank Acc. No. NM000343) instead of hSGLT2 cDNA is expressed in CHO-K1 or HEK293 cells.

Alternatively, measurement of the cellular membrane potential for hSGLT1 and hSGLT2 may also be used for the biological testing of substances. The cell models described earlier may be used for this. For the test, 10,000 cells per well of a black 384-well plate with a transparent base coated with poly-D-lysine are seeded in culture medium and incubated for 16 hours at 37° C. 5% $CO_2$. Then the cells are washed twice with glucose-free HBSS buffer (12.67 mol/l $CaCl_2$, 4.93 mmol/l $MgCl_2$, 4.07 mmol/l $MgSO_4$, 4.41 mmol/l $KH_2PO_4$; pH 7.4) and covered with 20 µl HBSS. After the addition of 20 µl of charging buffer (Membrane Potential Assay Kit Explorer $R^{8126}$, Molecular Devices GmbH, Ismaning) and 20 µl of the substance to be tested in a suitable concentration, incubation is continued for a further 30 min. at 37° C. 5% $CO_2$. The measurement is carried out in the Fluorescent Imaging Plate Reader (Molecular Devices GmbH, Ismaning) at an excitation wavelength of 485 nm and is started by the addition of 20 µl of stimulant buffer (140 mM NaCl and 120 mM glucose). The depolarisation of the cell caused by the glucose-induced influx of $Na^+$ can be measured and quantified as a change in fluorescence.

The compounds of general formula I according to the invention may for example have EC50 values of less than 1000 nM, particularly less than 200 nM, particularly preferably less than 50 nM.

In view of their ability to inhibit the SGLT activity, the compounds of general formula I according to the invention and the corresponding pharmaceutically acceptable salts thereof are theoretically suitable for the treatment and/or preventative treatment of all those conditions or diseases which may be affected by the inhibition of the SGLT activity, particularly the SGLT-2 activity. Therefore, compounds according to the invention are particularly suitable for the prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia. These substances are also suitable for preventing beta-cell degeneration such as e.g. apoptosis or necrosis of pancreatic beta cells. The substances are also suitable for improving or restoring the functionality of pancreatic cells, and also for increasing the number and size of pancreatic beta cells. The compounds according to the invention may also be used as diuretics or antihypertensives and are suitable for the prevention and treatment of acute renal failure.

In particular, the compounds according to the invention, including the physiologically acceptable salts thereof, are suitable for the prevention or treatment of diabetes, particularly type 1 and type 2 diabetes mellitus, and/or diabetic complications.

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 1 to 100 mg, preferably 1 to 30 mg, by intravenous route, and 1 to 1000 mg, preferably 1 to 100 mg, by oral route, in each case administered 1 to 4 times a day. For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, solutions, suspensions or suppositories.

The compounds according to the invention may also be used in conjunction with other active substances, particularly for the treatment and/or prevention of the diseases and conditions mentioned above. Other active substances which are suitable for such combinations include, in particular, those which potentiate the therapeutic effect of an SGLT antagonist according to the invention with respect to one of the indications mentioned and/or which allow the dosage of an SGLT antagonist according to the invention to be reduced. Therapeutic agents which are suitable for such a combination include, for example, antidiabetic agents such as metformin, sulphonylureas (e.g. glibenclamide, tolbutamide, glimepiride), nateglinide, repaglinide, thiazolidinediones (e.g. rosiglitazone, pioglitazone), PPAR-gamma-agonists (e.g. GI 262570) and antagonists, PPAR-gamma/alpha modulators (e.g. KRP 297), alpha-glucosidase inhibitors (e.g. acarbose, voglibose), DPPIV inhibitors (e.g. LAF237, MK-431), alpha2-antagonists, insulin and insulin analogues, GLP-1 and GLP-1 analogues (e.g. exendin-4) or amylin. Other active substances which are suitable as combination partners include inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenolpyruvate carboxykinase, glycogen synthase kinase or pyruvate dehydrokinase, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-increasing compounds such as, for example, CETP inhibitors or ABC1 regulators or active substances for treating obesity, such as perhaps sibutramine or tetrahydrolipostatin, dexfenfluramine, axokine, antagonists of the cannabinoid1 receptor, MCH-1 receptor antagonists, MC4 receptor agonists, NPY5 or NPY2 antagonists or $\beta^3$-agonists such as SB-418790 or AD-9677 and agonists of the 5HT2 c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan, cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramate, protein-kinase C inhibitors, advanced glycation end product inhibitors or aldose reductase inhibitors may be used for the treatment or prevention of complications of diabetes.

The dosage for the combination partners mentioned above is usefully ⅕ of the lowest dose normally recommended up to 1/1 of the normally recommended dose.

Therefore, in another aspect, this invention relates to the use of a compound according to the invention or a physiologically acceptable salt of such a compound combined with at least one of the active substances described above as a combination partner, for preparing a pharmaceutical composition which is suitable for the treatment or prevention of diseases or conditions which can be affected by inhibiting the sodium-dependent glucose cotransporter SGLT. These are preferably metabolic diseases, particularly one of the diseases or conditions listed above, most particularly diabetes or diabetic complications.

The use of the compound according to the invention, or a physiologically acceptable salt thereof, in combination with another active substance may take place simultaneously or at staggered times, but particularly within a short space of time. If they are administered simultaneously, the two active substances are given to the patient together; while if they are used at staggered times the two active substances are given to the patient one after the other within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

Thus, for example, a pharmaceutical composition according to the invention comprises a combination of a compound of formula I according to the invention or a physiologically acceptable salt of such a compound and at least one angiotensin II receptor antagonist optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

In the foregoing and following text, H atoms of hydroxyl groups are not explicitly shown in every case in structural formulae. The Examples that follow are intended to illustrate the present invention without restricting it:

Preparation of the Starting Compounds:

EXAMPLE I

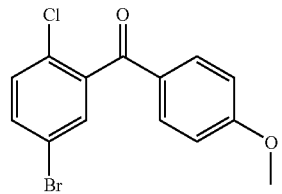

(5-bromo-2-chloro-phenyl)-(4-methoxy-phenyl)-methanone 38.3 ml oxalyl chloride and 0.8 ml of dimethylformamide are added to a mixture of 100 g 5-bromo-2-chloro-benzoic acid in 500 ml dichloromethane. The reaction mixture is stirred for 14 h, then filtered and separated from all the volatile constituents in the rotary evaporator. The residue is dissolved in 150 ml dichloromethane, the solution is cooled to −5° C., and 46.5 g anisol are added. Then 51.5 g aluminium trichloride are added batchwise so that the temperature does not exceed 5° C. The solution is stirred for another 1 h at 1-5° C. and then poured onto ice. The organic phase is separated off and the aqueous phase is extracted a further three times with dichloromethane. The combined organic phases are washed with aqueous 1 M hydrochloric acid, twice with 1 M sodium hydroxide solution and with saturated sodium chloride solution. Then the organic phase is dried, the solvent is removed and the residue is recrystallised in ethanol.

Yield: 86.3 g (64% of theory)

Mass spectrum (ESI$^+$): m/z=325/327/329 (bromine+chlorine) [M+H]$^+$

EXAMPLE II

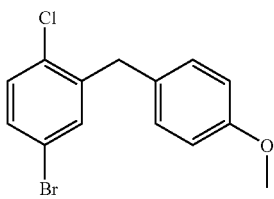

4-bromo-1-chloro-2-(4-methoxy-benzyl)-benzene

A solution of 86.2 g (5-bromo-2-chloro-phenyl)-(4-methoxy-phenyl)-methanone and 101.5 ml triethylsilane in 75 ml dichloromethane and 150 ml acetonitrile is cooled to 10° C. Then with stirring 50.8 ml boron trifluoride diethyl etherate are added such that the temperature does not exceed 20° C. The solution is stirred for 14 h at ambient temperature, before another 9 ml triethylsilane and 4.4 ml boron trifluoride diethyletherate are added. The solution is stirred for a further 3 h at 45-50° C. and then cooled to ambient temperature. A solution of 28 g potassium hydroxide in 70 ml of water is added and the mixture is stirred for 2 h. Then the organic phase is separated off and the aqueous phase is extracted another three times with diisopropylether. The combined organic phases are washed twice with 2 M potassium hydroxide solution and once with aqueous sodium chloride solution and then dried over sodium sulphate. After the solvent has been eliminated the residue is stirred in ethanol, separated off again and dried at 60° C.

Yield: 50.0 g (61% of theory)

Mass spectrum (ESI$^+$): m/z=310/312/314 (bromine+chlorine) [M+H]$^+$

EXAMPLE III

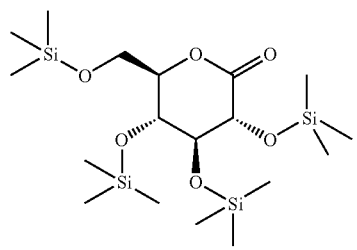

2,3,4,6-tetrakis-O-(trimethylsilyl)-D-glucopyranone

A solution of 20 g D-Glucono-1,5-lactone and 98.5 ml N-methylmorpholine in 200 ml of tetrahydrofuran is cooled to −5° C. Then 85 ml trimethylsilyl chloride are added dropwise so that the temperature does not exceed 5° C. The solution is then stirred for 1 h at ambient temperature, 5 h at 35° C. and for another 14 h at ambient temperature. After the addition of 300 ml of toluene the solution is cooled in the ice bath, and 500 ml of water are added such that the temperature does not exceed 10° C. The organic phase is then separated off and in each case washed once with aqueous sodium dihydrogen phosphate solution, water and saturated aqueous sodium chloride solution. The solvent is removed, the residue is taken up in 250 ml of toluene and the solvent is again totally eliminated.

Yield: 52.5 g (approx. 90% pure)

Mass spectrum (ESI$^+$): m/z=467 [M+H]$^+$

EXAMPLE IV

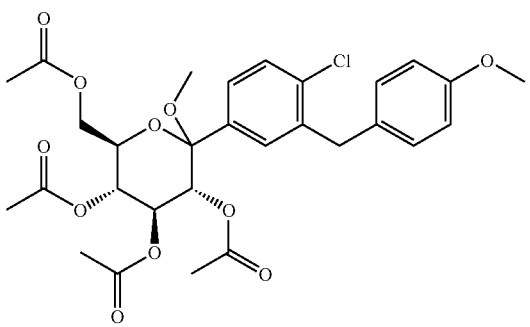

1-chloro-4-(2,3,4,6-tetra-O-acetyl-1-methoxy-D-glucopyranos-1-yl)-2-(4-methoxybenzyl)-benzene A solution of 1.0 g 4-bromo-1-chloro-2-(4-methoxy-benzyl)-benzene in 14 ml dry diethyl ether is cooled to −80° C. under argon. 4.0 ml of a 1.7 M solution of tert-butyllithium in pentane are slowly added dropwise to the cooled solution, and then the solution is stirred for 30 min at −80° C. This solution is then added dropwise through a transfer needle cooled with dry ice to a solution of 1.61 g 2,3,4,6-tetrakis-O-(trimethylsilyl)-D-glucopyranone in 10 ml diethyl ether which has been cooled to −80° C. The resulting solution is stirred for 4 h at −78° C. Then a solution of 0.4 ml methanesulphonic acid in 12 ml of methanol is added and the solution is stirred for 16 h at ambient temperature. The solution is then neutralised with ethyldiisopropylamine and evaporated down. The residue is taken up in toluene and again evaporated down. Then the residue is dissolved in 8 ml of toluene, and 3.4 ml ethyldiisopropylamine are added to the solution. The solution is cooled in the ice bath, and then 1.4 ml acetic anhydride and 0.04 g 4-dimethylaminopyridine are added. The solution is stirred for 6 h at ambient temperature and then combined with aqueous sodium hydrogen carbonate solution. The organic phase is separated off and the aqueous phase is extracted with ethyl acetate. After drying the combined organic extracts on sodium sulphate and removal of the solvent the residue is chromatographed on silica gel (cyclohexane/ethyl acetate 6:1→1:1).

Yield: 1.55 g (85% of theory)

Mass spectrum (ESI$^+$): m/z=610/612 (chlorine) [M+NH$_4$]$^+$

EXAMPLE V

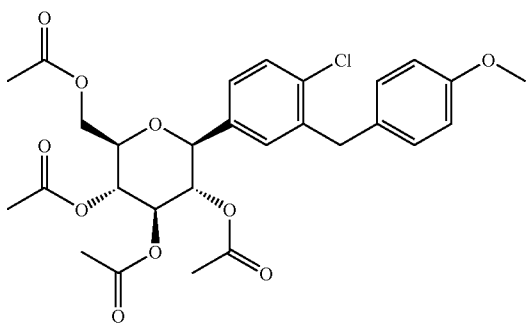

1-chloro-4-(2,3,4,6-tetra-O-acetyl-β-D-glucopyranos-1-yl)-2-(4-methoxy-benzyl)-benzene A solution of 1.44 g 1-chloro-4-(2,3,4,6-tetra-O-acetyl-1-methoxy-D-glucopyranosyl)-2-(4-methoxybenzyl)-benzene in 20 ml acetonitrile and 44 μl water is cooled in the ice bath. Then 1.2 ml triethylsilane and 0.26 ml boron trifluoride diethyl etherate are added. The solution is stirred for 1 h in the ice bath and then at ambient temperature. After 3 and 5 h another 0.72 ml triethylsilane and 0.15 ml boron trifluoride diethyl etherate are added. After a further 12 h stirring at ambient temperature aqueous sodium hydrogen carbonate solution is added, the mixture is stirred for 0.5 h and then extracted with ethyl acetate. The organic phase is dried over sodium sulphate, concentrated and chromatographed on silica gel (cyclohexane/ethyl acetate 8:1→1:1). If the product is still not isomerically pure, it may be purified by recrystallisation in ethanol of the isomers.

Yield: 1.12 g (82% of theory)
Mass spectrum (ESI⁺): m/z=580/582 (chlorine) [M+NH$_4$]⁺

EXAMPLE VI

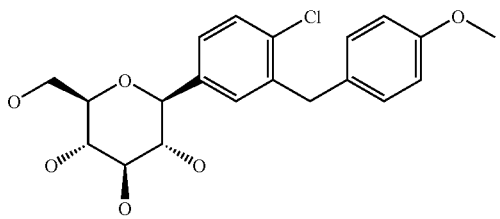

1-chloro-2-(4-methoxy-benzyl)-4-(1-β-D-glucopyranosyl)-benzene 2 ml 4 M potassium hydroxide solution are added to a solution of 1.00 g 1-chloro-4-(2,3,4,6-tetra-O-acetyl-β-D-glucopyranos-1-yl)-2-(4-methoxy-benzyl)-benzene in 20 ml of methanol. The solution is stirred for 8 h at ambient temperature and then neutralised with 1 M hydrochloric acid. The solution is freed from methanol, combined with aqueous sodium chloride solution and extracted with ethyl acetate. The organic phase is dried over sodium sulphate and the solvent is eliminated. The residue is purified through silica gel (dichloromethane/methanol 1:0→3:1).

Yield: 0.64 g (91% of theory)
Mass spectrum (ESI⁺): m/z=412/414 (chlorine) [M+NH$_4$]⁺

EXAMPLE VII

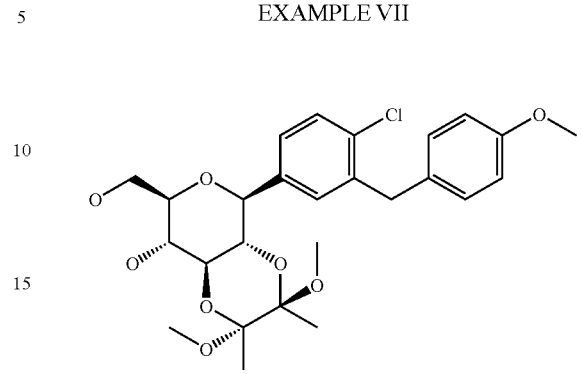

1-chloro-2-(4-methoxy-benzyl)-4-[2,3-O-(2,3-dimethoxy-buta-2,3-diyl)-β-D-glucopyranos-1-yl]-benzene 0.49 ml butane-2,3-dione, 1.2 ml methyl orthoformate and 0.64 ml boron trifluoride diethyl etherate are added successively to a solution, heated to 60° C., of 1.0 g 1-chloro-2-(4-methoxy-benzyl)-4-(1-β-D-glucopyranosyl)-benzene in 14 ml of methanol. The solution is stirred for 4 h at 60° C. and then cooled to ambient temperature. At ambient temperature 3 ml triethylamine are added, and the solution is stirred for another 0.5 h. Then the solution is evaporated down and the residue is purified through silica gel (cyclohexane/ethyl acetate 4:1→1:1).

Yield: 0.70 g (54% of theory), and additionally the 3,4-protected glucose derivative (0.54 g, 42% of theory) is isolated.
Mass spectrum (ESI⁺): m/z=526/528 (chlorine) [M+NH$_4$]⁺

EXAMPLE VIII

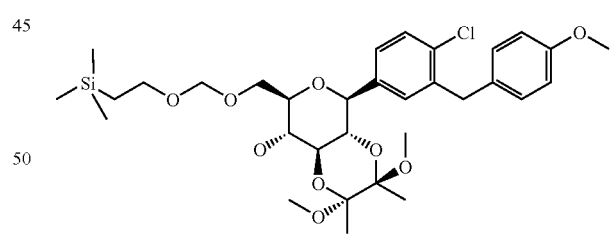

1-chloro-2-(4-methoxy-benzyl)-4-[2,3-O-(2,3-dimethoxy-buta-2,3-diyl)-6-O-(2-trimethylsilylethoxymethyl)-β-D-glucopyranos-1-yl]-benzene 0.72 ml 2-trimethylsilylethoxymethyl chloride are added to a solution of 2.08 g 1-chloro-2-(4-methoxy-benzyl)-4-[2, 3-O-(2,3-dimethoxy-buta-2,3-diyl)-β-D-glucopyranos-1-yl]-benzene and 0.8 ml ethyldiisopropylamine in 15 ml dichloromethane. After 8 h stirring at ambient temperature a further 0.3 ml ethyldiisopropylamine and 0.2 ml 2-trimethylsilylethoxymethyl chloride are added and the mixture is stirred for a further 5 h at ambient temperature. Then the reaction solution is combined with water and extracted with dichloromethane. The combined organic extracts are dried over sodium sulphate, and the solvent is removed. The residue is chromatographed on silica gel (cyclohexane/ethyl acetate 1:0→3:2).

Yield: 1.50 g (58% of theory)
Mass spectrum (ESI+): m/z=656/658 (chlorine) [M+NH4]+

EXAMPLE IX

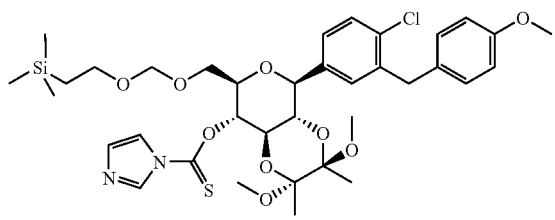

1-chloro-2-(4-methoxy-benzyl)-4-[2,3-O-(2,3-dimethoxy-buta-2,3-diyl)-4-O-(imidazol-1-yl-thiocarbonyl)-6-O-(2-trimethylsilylethoxymethyl)-β-D-glucopyranos-1-yl]-benzene A solution of 0.3 g 1-chloro-2-(4-methoxy-benzyl)-4-[2,3-O-(2,3-dimethoxy-buta-2,3-diyl)-6-O-(2-trimethylsilylethoxymethyl)-β-D-glucopyranos-1-yl]-benzene and 0.21 g thiocarbonyldiimidazole in 5 ml of toluene is stirred for 5 h at 90° C. Then the reaction solution is combined with water and extracted with ethyl acetate. The combined organic extracts are dried over sodium sulphate, and the solvent is removed. The residue is chromatographed on silica gel (cyclohexane/ethyl acetate 1:0→1:1).

Yield: 0.22 g (63% of theory)
Mass spectrum (ESI+): m/z=7491751 (chlorine) [M+H]+

EXAMPLE X

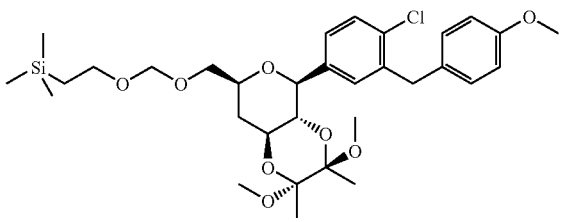

1-chloro-2-(4-methoxy-benzyl)-4-[2,3-O-(2,3-dimethoxy-buta-2,3-diyl)-4-desoxy-6-O-(2-timethylsilylethoxymethyl)-β-D-glucopyranos-1-yl]-benzene A solution of 0.22 g 1-chloro-2-(4-methoxy-benzyl)-4-[2,3-O-(2,3-dimethoxy-buta-2,3-diyl)-4-O-(imidazol-1-yl-thiocarbonyl)-6-O-(2-trimethylsilylethoxymethyl)-β-D-glucopyranos-1-yl]-benzene in 1.4 ml tris(trimethylsilyl)silane and 3 ml of toluene is flushed with argon. Then 17 mg azobisisobutyronitrile are added, and the solution is stirred overnight at 120° C. After cooling to ambient temperature methanol is added and the solution is evaporated down. 1 M hydrochloric acid is added to the residue which is then extracted with ethyl acetate. The combined organic extracts are dried over sodium sulphate, and the solvent is removed. The residue is chromatographed on silica gel (cyclohexane/ethyl acetate 1:0→3:2).

Yield: 0.15 g (80% of theory)
Mass spectrum (ESI+): m/z=640/642 (chlorine) [M+H]+

EXAMPLE XI

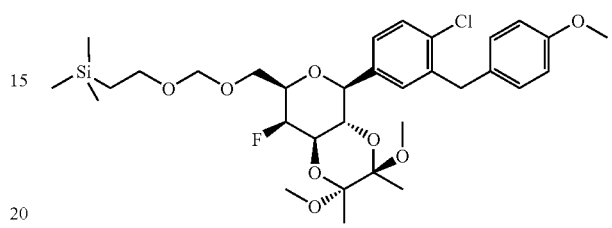

1-chloro-2-(4-methoxy-benzyl)-4-[2,3-O-(2,3-dimethoxy-buta-2,3-diyl)-4-desoxy-4-fluoro-6-O-(2-trimethylsilylethoxymethyl)-β-D-galactopyranos-1-yl]-benzene 0.3 ml [bis(2-methoxyethyl)amino]sulphur trifluoride are added to a solution of 0.2 g 1-chloro-2-(4-methoxy-benzyl)-4-[2,3-O-(2,3-dimethoxy-buta-2,3-diyl)-6-O-(2-trimethylsilylethoxymethyl)-β-D-glucopyranos-1-yl]-benzene in 2 ml dichloromethane cooled to −30° C. The solution is allowed to come up slowly to ambient temperature and then stirred for another 16 h at ambient temperature. The solution is then cooled in the ice bath, diluted with dichloromethane and combined with aqueous sodium hydrogen carbonate solution. The organic phase is separated off and the organic phase is extracted with dichloromethane. The combined organic phases are dried over sodium sulphate, and the solvent is removed. The residue is chromatographed on silica gel (cyclohexane/ethyl acetate 1:0→2:3).

Yield: 40 mg (20% of theory)
Mass spectrum (ESI+): m/z=658/660 (chlorine) [M+NH4]+

Preparation of the End Compounds:

EXAMPLE 1

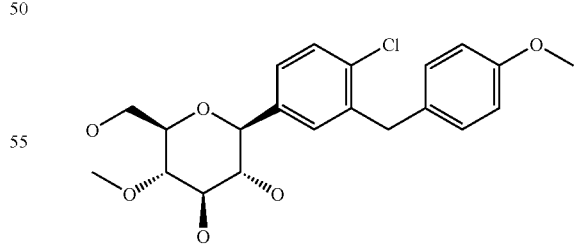

1-chloro-2-(4-methoxy-benzyl)-4-(4-O-methyl-β-D-glucopyranos-1-yl)-benzene 0.14 g silver(I)oxide and 70 μl methyl iodide are added to a solution of 0.35 g 1-chloro-2-(4-methoxy-benzyl)-4-[2,3-O-(2,3-dimethoxy-buta-2,3-diyl)-β-D-glucopyranos-1-yl]- benzene in 2.5 ml of dimethylformamide. The mixture is stirred for 48 h at ambient temperature and then diluted with ethyl acetate. Then the mixture is filtered through Celite, water is added and extracted with ethyl acetate. After drying over sodium sulphate the solvent is removed and the residue is chromatographed on silica gel (cyclohexane/ethyl acetate 5:1→1:1). The 1-chloro-2-(4-methoxy-benzyl)-4-[2,3-O-(2, 3-dimethoxy-buta-2,3-diyl)-4-O-methyl-β-D-glucopyranos-1-yl]-benzene thus obtained is taken up in 2.5 ml of a mixture of trifluoroacetic acid/water (80:20) and the solution is stirred for 1 h at ambient temperature. The solution is diluted with water and made alkaline with 4 M potassium hydroxide solution. The aqueous solution is extracted with ethyl acetate, the combined extracts are dried over sodium sulphate and the solvent is removed. The residue is chromatographed on silica gel (dichloromethane/methanol 1:0→8:1).

Yield: 0.12 g (43% of theory)

Mass spectrum (ESI$^+$): m/z=426/428 (chlorine) [M+NH$_4$]$^+$

EXAMPLE 2

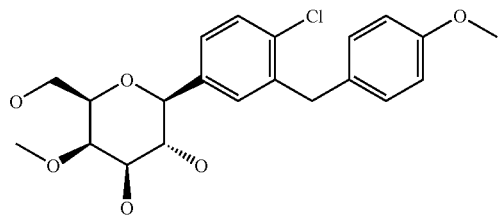

1-chloro-2-(4-methoxy-benzyl)-4-(4-O-methyl-β-D-galactopyranos-1-yl)-benzene

Starting from 1-chloro-2-(4-methoxy-benzyl)-4-[2,3-O-(2,3-dimethoxy-buta-2,3-diyl)-β-D-galactopyranos-1-yl]-benzene, which may be obtained analogously to the preceding Examples, after protecting the 6-OH function with an acid-labile protective group, such as e.g. methoxymethyl or 2-trimethylsilylethoxymethyl, and according to the reaction described in Example 1, 1-chloro-2-(4-methoxy-benzyl)-4-(4-O-methyl-β-D-galactopyranos-1-yl)-benzene is obtained.

EXAMPLE 3

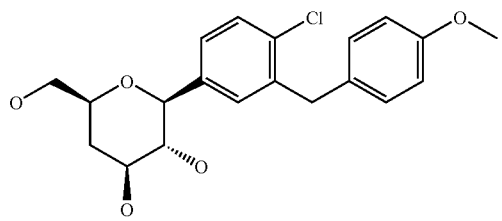

1-chloro-2-(4-methoxy-benzyl)-4-(4-desoxy-β-D-glucopyranos-1-yl)-benzene

A solution of 0.15 g 1-chloro-2-(4-methoxy-benzyl)-4-[2, 3-O-(2,3-dimethoxy-buta-2,3-diyl)-4-desoxy-6-O-(2-trimethylsilylethoxymethyl)-β-D-glucopyranos-1-yl]-benzene in a trifluoroacetic acid/water mixture (80:20) is stirred for 30 min at ambient temperature. The solution is then diluted with water and made alkaline with 4 M potassium hydroxide solution. The aqueous solution is extracted with ethyl acetate, the combined extracts are dried over sodium sulphate and the solvent is eliminated. The residue is chromatographed on silica gel (dichloromethane/methanol 1:0→4:1).

Yield: 0.12 g (43% of theory)

Mass spectrum (ESI$^+$): m/z=396/398 (chlorine) [M+NH$_4$]$^+$

The following compound may be obtained analogously to Example 3:

(4) 1-chloro-2-(4-methoxy-benzyl)-4-(4-desoxy-4-fluoro-β-D-galactopyranos-1-yl)-benzene

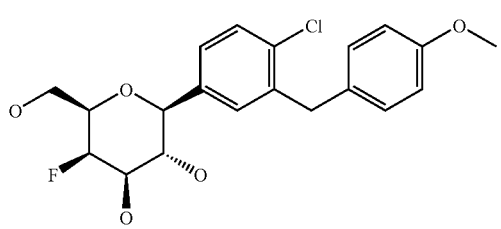

The following compounds are also prepared analogously to the foregoing Examples and other methods known from the literature:

| Ex. | Structure |
|---|---|
| (5) | ![structure] |
| (6) | ![structure] |
| (7) | ![structure] |

-continued
| Ex. | Structure |
|---|---|
| (8) | 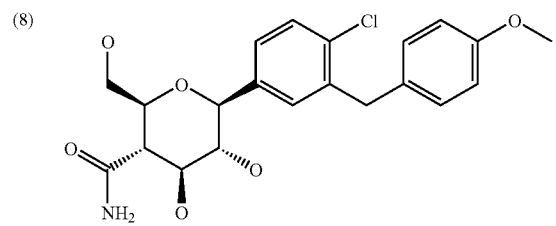 |
| (9) | 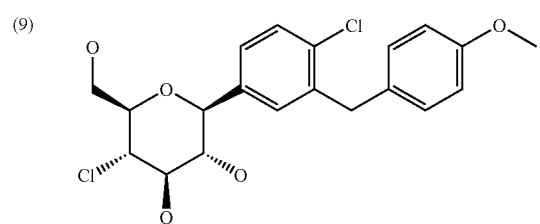 |
| (10) | 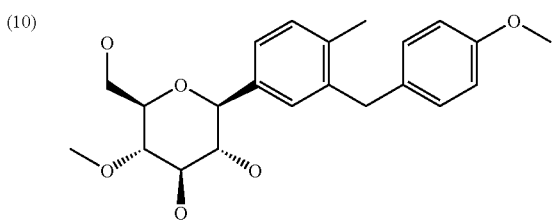 |
| (11) | 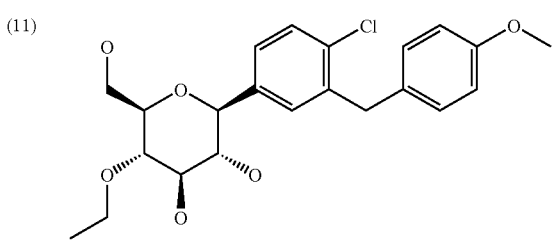 |
| (12) | 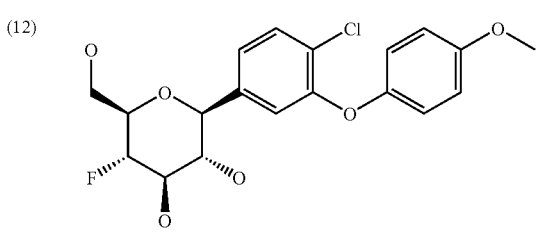 |
| (13) | 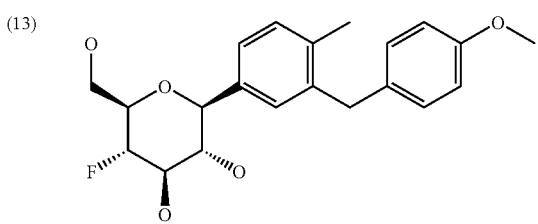 |
-continued
| Ex. | Structure |
|---|---|
| (14) | 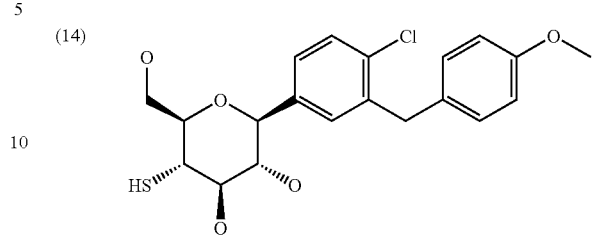 |
| (15) | 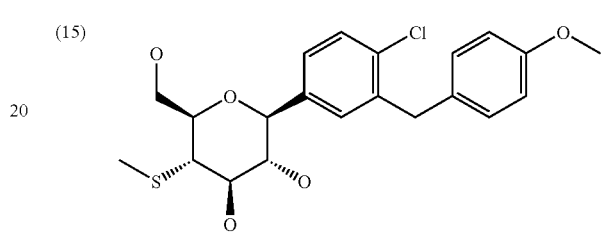 |
| (16) | 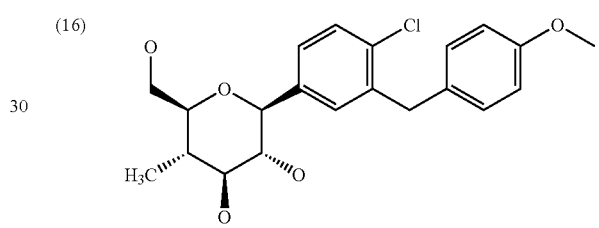 |
| (17) | 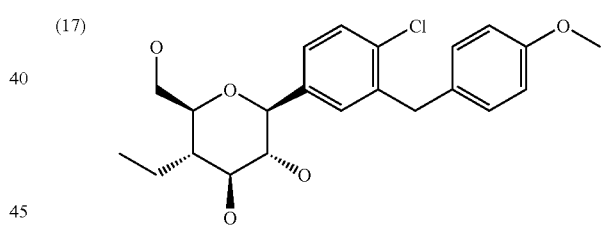 |
| (18) | 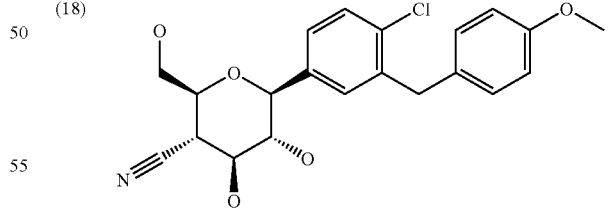 |
| (19) | 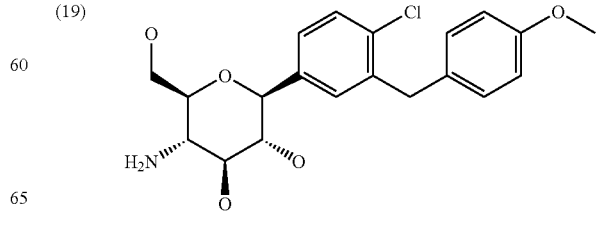 |

| Ex. | Structure |
|---|---|
| (20) | 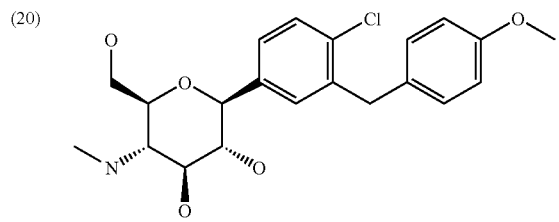 |
| (21) | 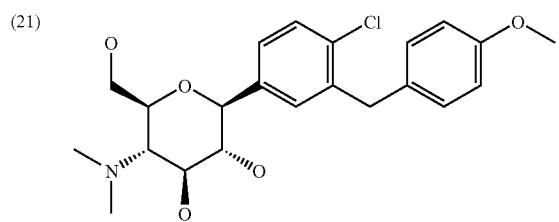 |
| (22) | 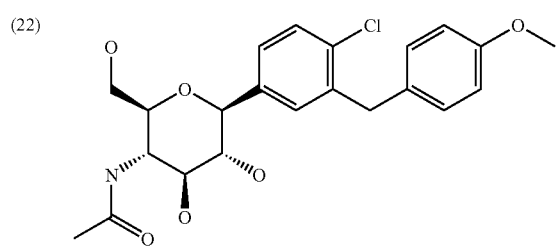 |
| (23) | 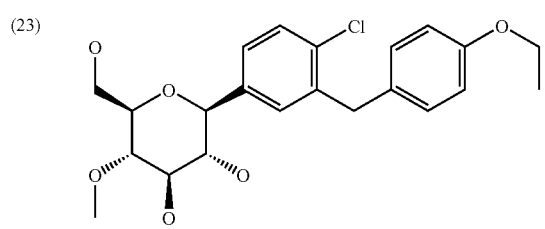 |
| (24) | 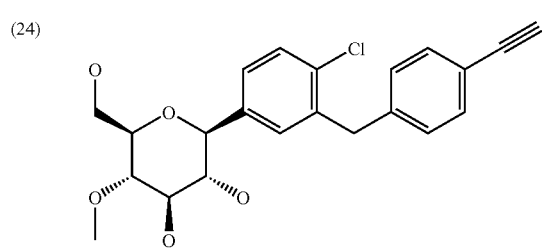 |
| (25) | 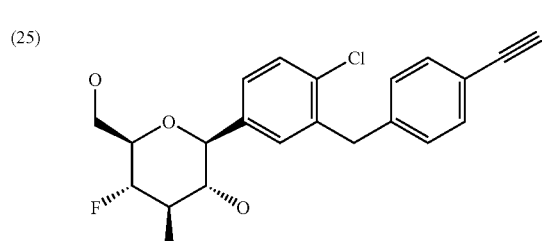 |
| Ex. | Structure |
|---|---|
| (26) | 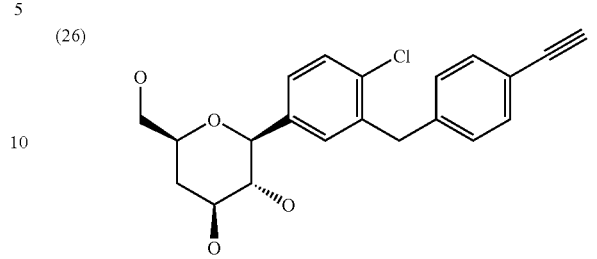 |
| (27) | 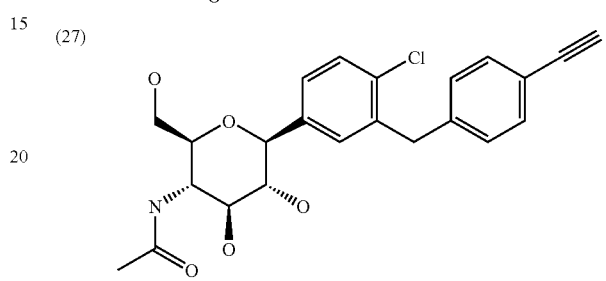 |
| (28) | 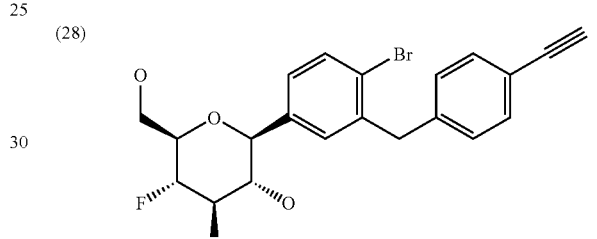 |
| (29) | 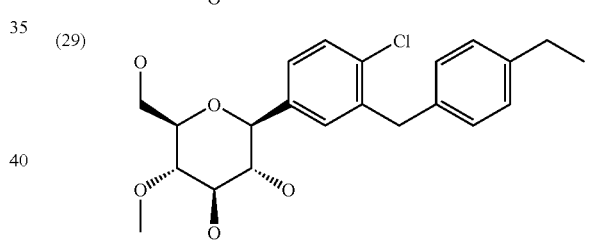 |
| (30) | 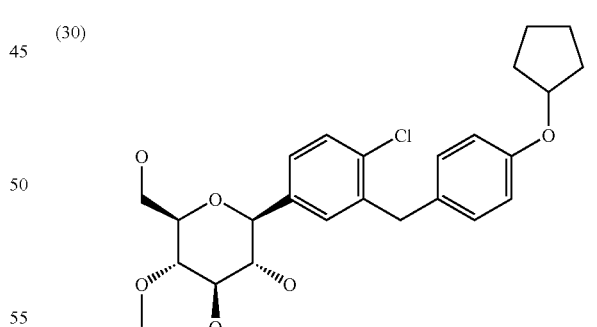 |
| (31) | 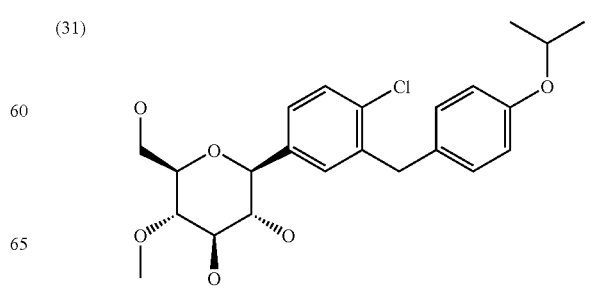 |

-continued
| Ex. | Structure |
|---|---|
| (32) | 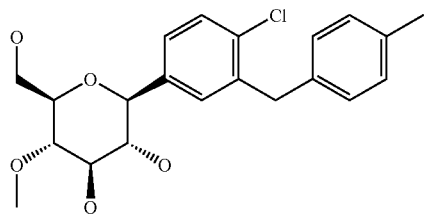 |
| (33) | 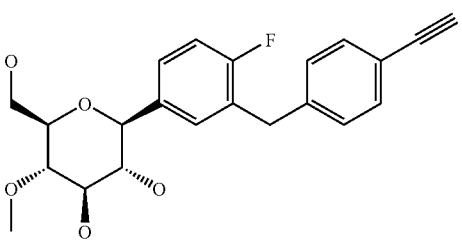 |
| (34) | 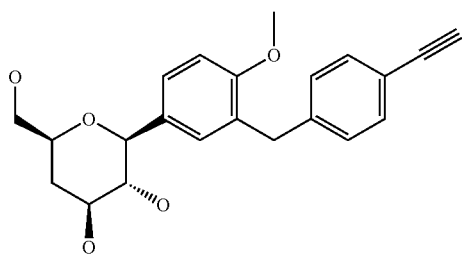 |
| (35) | 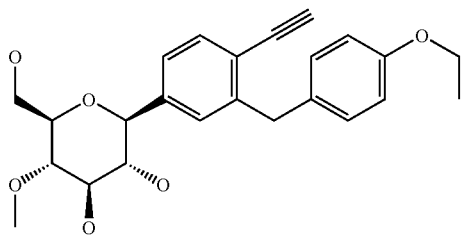 |
| (36) | 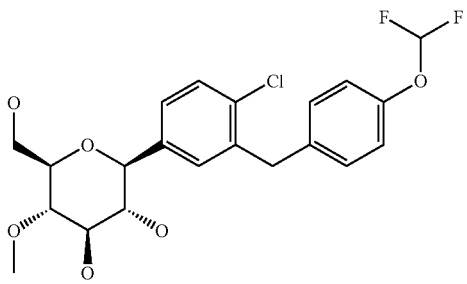 |
| (37) | 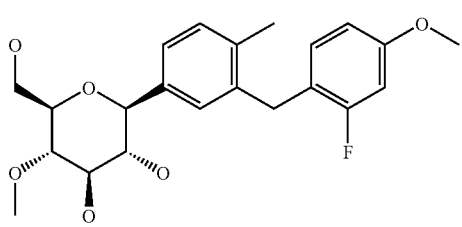 |
-continued
| Ex. | Structure |
|---|---|
| (38) | 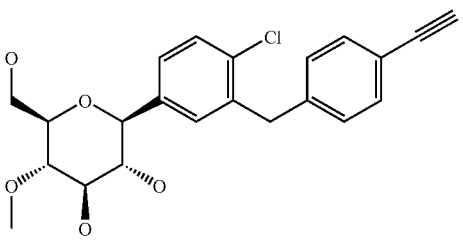 |
| (39) | 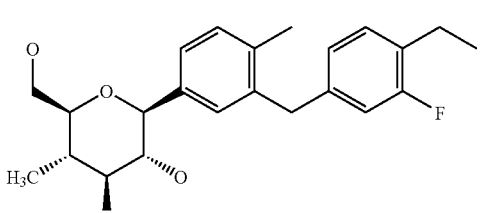 |
| (40) | 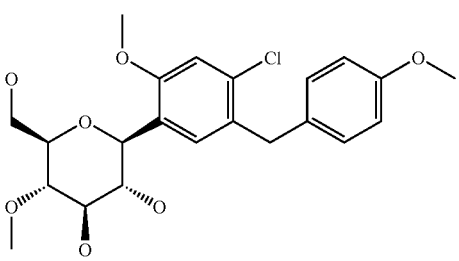 |
| (41) | 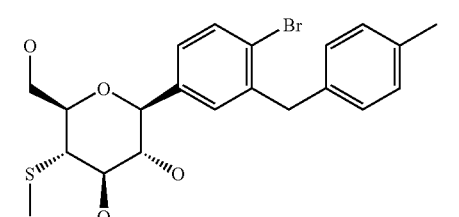 |
| (42) | 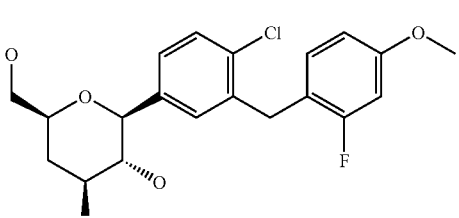 |
| (43) | 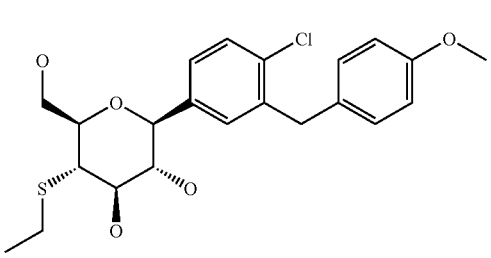 |

-continued

| Ex. | Structure |
|---|---|
| (44) | [chemical structure with Cl, OMe, sulfone, and pyranose ring] |

The following are examples of formulations in which the phrase "active substance" denotes one or more compounds according to the invention, including the salts thereof. In the case of one of the combinations mentioned above with one or more other active substances the term "active substance" also includes the additional active substances.

EXAMPLE A

Tablets Containing 100 mg of Active Substance
Composition:

| 1 tablet contains: | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:
The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

| Weight of tablet: | 220 mg |
|---|---|
| Diameter: | 10 mm, biplanar, facetted on both sides and notched on one side. |

EXAMPLE B

Tablets Containing 150 mg of Active Substance
Composition:

| 1 tablet contains: | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:
The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

| Weight of tablet: | 300 mg |
|---|---|
| die: | 10 mm, flat |

EXAMPLE C

Hard Gelatine Capsules Containing 150 mg of Active Substance
Composition:

| 1 capsule contains: | | |
|---|---|---|
| active substance | | 150.0 mg |
| corn starch (dried) | approx. | 180.0 mg |
| powdered lactose | approx. | 87.0 mg |
| magnesium stearate | | 3.0 mg |
| | approx. | 420.0 mg |

Preparation:
The active substance is mixed with the excipients, passed through a screen with a mesh size of 0.75 mm and homogeneously mixed using a suitable apparatus. The finished mixture is packed into size 1 hard gelatine capsules.

| Capsule filling: | approx. 320 mg |
|---|---|
| Capsule shell: | size 1 hard gelatine capsule. |

EXAMPLE D

Suppositories Containing 150 mg of Active Substance
Composition:

| 1 suppository contains: | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:
After the suppository mass has been melted the active substance is homogeneously distributed therein and the melt is poured into chilled moulds.

EXAMPLE E

Ampoules Containing 10 mg Active Substance
Composition:

| active substance | | 10.0 mg |
|---|---|---|
| 0.01 N hydrochloric acid q.s. | | |
| double-distilled water | ad | 2.0 ml |

Preparation:

The active substance is dissolved in the necessary amount of 0.01 N HCl, made isotonic with common salt, filtered sterile and transferred into 2 ml ampoules.

EXAMPLE F

Ampoules Containing 50 mg of Active Substance
Composition:

| active substance | | 50.0 mg |
|---|---|---|
| 0.01 N hydrochloric acid q.s. | | |
| double-distilled water | ad | 10.0 ml |

Preparation:

The active substance is dissolved in the necessary amount of 0.01 N HCl, made isotonic with common salt, filtered sterile and transferred into 10 ml ampoules.

The invention claimed is:

1. A D-pyranosyl-substituted phenyl compound of general formula I

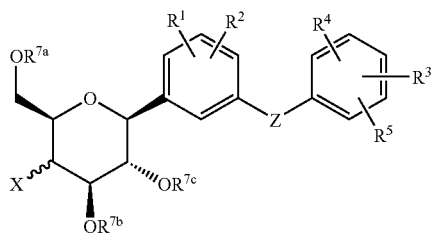

I wherein $R^1$ denotes hydrogen, fluorine, chlorine, bromine, iodine, $C_{1-6}$-alkyl, $C_{2-6}$-alkynyl, $C_{2-6}$-alkenyl, $C_{3-10}$-cycloalkyl, $C_{3-10}$-cycloalkyl-$C_{1-3}$-alkyl, $C_{5-10}$-cycloalkenyl, $C_{5-10}$-cycloalkenyl-$C_{1-3}$-alkyl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperizin-1-ylcarbonyl, $C_{1-4}$-alkoxycarbonyl, amino, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$alkyl)piperazin-1-yl, $C_{1-4}$-alkylcarbonylamino, $C_{1-6}$-alkyloxy, $C_{3-10}$-cycloalkyloxy, $C_{5-10}$-cycloalkenyloxy, aryloxy, $C_{1-4}$-alkylsulphanyl, $C_{1-4}$-alkylsulphinyl, $C_{1-4}$-alkylsulphonyl, $C_{3-10}$-cycloalkylsulphanyl, $C_{3-10}$cycloalkylsulphinyl, $C_{3-10}$-cycloalkylsulphonyl, $C_{5-10}$-cycloalkenylsulphanyl, $C_{5-10}$-cycloalkenylsulphinyl, $C_{5-10}$-cycloalkenylsulphonyl, arylsulphanyl, arylsulphinyl, arylsulphonyl, hydroxy, cyano or nitro, while alkyl, alkenyl, alkynyl, cycloalkyl and cycloalkenyl groups may be partly or completely fluorinated or may be mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be replaced by CO or $SO_2$, and $R^2$ denotes hydrogen, fluorine, chlorine, bromine, hydroxy, $C_{1-4}$-alkyl, $C_{1-4}$-alkoxy, cyano or nitro, while alkyl groups may be mono- or polysubstituted by fluorine, or in the event that $R^1$ and $R^2$ are bound to two adjacent C atoms of the phenyl ring, $R^1$ and $R^2$ may be joined together such that $R^1$ and $R^2$ together form a $C_{3-5}$-alkylene, $C_{3-5}$-alkenylene or butadienylene bridge, which may be partly or completely fluorinated or may be mono- or disubstituted by identical or different substituents selected from chlorine, hydroxy, $C_{1-3}$-alkoxy and $C_{1-3}$-alkyl, and wherein one or two methylene groups may be replaced independently of one another by O, S, CO, SO, $SO_2$ or $NR^N$, and wherein in the case of a butadienylene bridge one or two methyne groups may be replaced by an N atom, $R^3$ denotes hydrogen, fluorine, chlorine, bromine, iodine, $C_{1-6}$-alkyl, $C_{2-6}$-alkynyl, $C_{2-6}$-alkenyl, $C_{3-10}$-cycloalkyl, $C_{3-10}$-Cycloalkyl-$C_{1-3}$-alkyl, $C_{5-10}$-cycloalkenyl, $C_{5-10}$-cycloalkenyl-$C_{1-3}$-alkyl, aryl, heteroaryl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl) aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperazin-1-ylcarbonyl, hydroxycarbonyl, $C_{1-4}$-alkoxycarbonyl, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$-alkyl) piperazin-1-yl, $C_{1-4}$-alkylcarbonylamino, arylcarbonylamino, heteroaryl-carbonylamino, $C_{1-4}$-alkylsulphonylamino, arylsulphonylamino, $C_{1-6}$-alkoxy, $C_{3-7}$-cycloalkyloxy, $C_{5-7}$-cycloalkenyloxy, aryloxy, heteroaryloxy, $C_{1-4}$-alkyl-sulphanyl, $C_{1-4}$-alkylsulphinyl, $C_{1-4}$-alkylsulphonyl, $C_{3-10}$-cycloalkylsulphanyl, $C_{3-10}$-cycloalkylsulphinyl, $C_{3-10}$-cycloalkylsulphonyl, $C_{5-10}$-cycloalkenylsulphanyl, $C_{5-10}$-cycloalkenylsulphinyl, $C_{5-10}$-cycloalkenylsulphonyl, arylsulphanyl, arylsulphinyl, arylsulphonyl, amino, hydroxy, cyano or nitro, while alkyl, alkenyl, alkynyl, cycloalkyl- and cycloalkenyl groups may be partly or completely fluorinated or mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be substituted by CO or $SO_2$, and $R^4$ independently of one another denote hydrogen, fluorine, chlorine, bromine, iodine, cyano, nitro, $C_{1-3}$-alkyl, $C_{1-3}$-alkoxy or methyl or methoxy substituted by 1 to 3 fluorine atoms, or if $R^3$ and $R^4$ are bound to two adjacent C atoms of the phenyl ring, $R^3$ and $R^4$ may be joined together such that $R^3$ and $R^4$ together form a $C_{3-5}$-alkylene, $C_{3-5}$-alkenylene or butadienylene bridge, which may be partly or completely fluorinated or mono- or disubstituted by identical or different substituents selected from chlorine, hydroxy, $C_{1-3}$-alkoxy and $C_{1-3}$-alkyl, and wherein one or two methylene groups may be replaced independently of one another by O, S, CO, SO, $SO_2$ or $NR^N$, and wherein in the case of a butadienylene bridge one or two methyne groups may be replaced by an N atom, $R^5$ independently of one another denote hydrogen, fluorine, chlorine, bromine, iodine, cyano, nitro, $C_{1-3}$-alkyl, $C_{1-3}$-alkoxy or methyl or methoxy substituted by 1 to 3 fluorine atoms, and $R^N$ denotes H, $C_{1-4}$-alkyl or $C_{1-4}$-alkylcarbonyl, L are selected independently of one another from among fluorine, chlorine, bromine, iodine, $C_{1-3}$-alkyl, difluoromethyl, trifluoromethyl, $C_{1-3}$-alkoxy, difluoromethoxy, trifluoromethoxy and cyano, $R^{7a}$, $R^{7b}$, $R^{7c}$ independently of one another have a meaning selected from among hydrogen, $(C_{1-18}$-alkyl)carbonyl, $(C_{1-18}$-alkyl)oxycarbonyl, arylcarbonyl and aryl-$(C_{1-3}$-alkyl)-carbonyl, X is hydrogen, chlorine, cyano, $C_{1-6}$-alkyl, $C_{2-6}$-alkynyl, $C_{2-6}$-alkenyl, $C_{1-6}$-alkylsulphonyl, hydroxycarbonyl, $C_{1-4}$-alkoxycarbonyl, aminocarbonyl or $C_{1-4}$alkylaminocarbonyl, while alkyl groups may be mono- or polyfluorinated or monosubstituted by hydroxy or cyano; or X is mercapto, $C_{1-5}$-alkylsulphanyl, $C_{2-5}$-alkenylsulphanyl, $C_{2-5}$-alkynylsulphanyl, $C_{3-7}$-cycloalkylsulphanyl or arylsulphanyl; or X is amino, $C_{1-5}$-alkylamino, N—$(C_{1-5}$-alkyl)-N—$(C_{1-3}$-alkyl)-amino, $C_{1-4}$-alkylcarbonylamino, N—$(C_{1-5}$-alkyl)-N—$(C_{1-4}$-alkylcarbonyl)-amino or arylamino; or X is fluorine; or X denotes bromine, iodine, $C_{1-6}$-alkylsulphonyloxy, arylsulphonyloxy or aryl-$C_{1-3}$-alkyl-sulphonyloxy, while the above-mentioned alkyl groups may be partly or completely fluorinated or mono- or dichlorinated and the above-mentioned aryl groups may be mono- or disubstituted by identical or different groups L, and Z denotes oxygen, methylene, dimethylmethylene, 1,1-cyclopropylene, difluoromethylene or carbonyl;

while by the aryl groups mentioned in the definition of the above-mentioned groups are meant phenyl or naphthyl groups, which may be mono- or disubstituted independently of one another by identical or different groups L; and by the heteroaryl groups mentioned in the definition of the above-mentioned groups are meant a pyrrolyl, furanyl, thienyl, pyridyl, indolyl, benzofuranyl, benzothiophenyl, quinolinyl or isoquinolinyl group, or a pyrrolyl, furanyl, thienyl or pyridyl group, wherein one or two methyne groups are replaced by nitrogen atoms, or an indolyl, benzofuranyl, benzothiophenyl, quinolinyl or isoquinolinyl group, wherein one to three methyne groups are replaced by nitrogen atoms, while the above-mentioned heteroaryl groups may independently of one another be mono- or disubstituted by identical or different groups L;

while by the N-heterocycloalkyl group mentioned in the definition of the above-mentioned groups is meant a saturated carbocyclic ring which comprises an imino group in the ring, which may comprise a further imino group or an O or S atom in the ring, and unless otherwise stated, the above-mentioned alkyl groups may be straight-chain or branched, the tautomers, the mixtures thereof and the physiologically acceptable salts thereof.

2. A D-pyranosyl-substituted phenyl compound of claim 1 according to formula IA

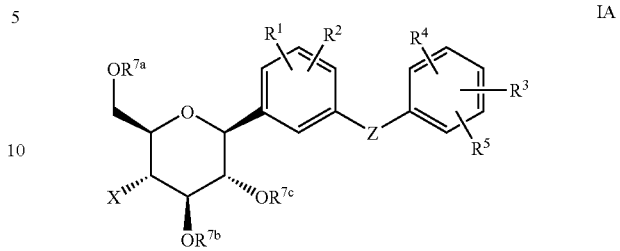

wherein $R^1$ to $R^5$, X, Z, $R^{7a}$, $R^{7b}$, $R^{7c}$ have the meanings according to claim 1.

3. A D-pyranosyl-substituted phenyl of claim 1, according to formula IA.2

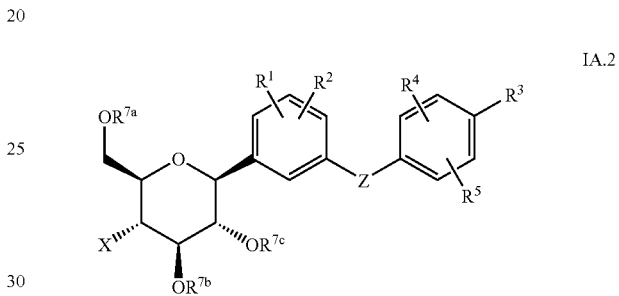

wherein $R^1$ to $R^5$, X, Z, $R^{7a}$, $R^{7b}$, $R^{7c}$ have the meanings according to claim 1.

4. A D-pyranosyl-substituted phenyl compound of claim 1, wherein:

$R^1$ denotes hydrogen, fluorine, chlorine, bromine, iodine, $C_{1-6}$-alkyl, $C_{2-6}$-alkynyl, $C_{2-6}$-alkenyl, $C_{3-7}$-cycloalkyl, $C_{5-7}$-cycloalkenyl, $C_{1-4}$-alkylcarbonyl, aminocarbonyl, $C_{1-4}$-alkylaminocarbonyl, di-$(C_{1-3}$-alkyl)aminocarbonyl, $C_{1-4}$-alkoxycarbonyl, $C_{1-4}$-alkylamino, di-$(C_{1-3}$-alkyl)amino, pyrrolidin-1-yl, piperidin-1-yl, morpholin-4-yl, $C_{1-4}$-alkylcarbonylamino, $C_{1-6}$-alkyloxy, $C_{3-7}$-cycloalkyloxy, $C_{5-7}$-cycloalkenyloxy, $C_{1-4}$-alkylsulphanyl, $C_{1-4}$-alkylsulphonyl, $C_{3-7}$-cycloalkylsulphanyl, $C_{3-7}$-cycloalkylsulphonyl, $C_{5-7}$-cycloalkenylsulphanyl, $C_{5-7}$-cycloalkenylsulphonyl, hydroxy or cyano, while alkyl, alkenyl, alkynyl, cycloalkyl and cycloalkenyl groups may be partly or completely fluorinated or mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, , and in N-heterocycloalkyl groups a methylene group may be replaced by CO or $SO_2$.

5. A D-pyranosyl-substituted phenyl compound of claim 1, wherein:

$R^3$ denotes hydrogen, fluorine, chlorine, bromine, $C_{1-6}$-alkyl, $C_{2-6}$-alkynyl, $C_{2-6}$-alkenyl, $C_{3-7}$-cycloalkyl, $C_{3-7}$-cycloalkyl-methyl, $C_{5-7}$-cycloalkenyl, $C_{3-7}$-cycloalkenyl-methyl, aryl, heteroaryl, $C_{1-4}$-alkylcarbonyl, aminocarbonyl, $C_{1-4}$-alkylaminocarbonyl, di-$(C_{1-3}$-alkyl)aminocarbonyl, $C_{1-4}$-alkoxycarbonyl, di-$(C_{1-3}$-alkyl)amino, pyrrolidin-1-yl, piperidin-1-yl, morpholin-4-yl, $C_{1-4}$-alkylcarbonyl-amino, $C_{1-6}$-alkoxy, $C_{3-7}$-cyclo-alkyloxy, $C_{5-7}$-cycloalkenyloxy, aryloxy, heteroaryloxy, $C_{1-4}$-alkylsulphanyl, $C_{1-4}$-alkylsulphonyl, $C_{3-7}$-cycloalkylsulphanyl, $C_{3-7}$-cycloalkylsulphonyl, $C_{5-7}$-cycloalkenylsulphanyl, $C_{5-7}$-cycloalkenylsulphonyl, hydroxy or cyano, while alkyl, alkenyl, alkynyl, cycloalkyl and cycloalkenyl groups may be partly or completely fluorinated or mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be replaced by CO or $SO_2$, the terms aryl and heteroaryl are as hereinbefore defined and aryl and heteroaryl groups may independently of one another be mono- or disubstituted by identical or different groups L, where L is defined as in claim 1.

6. A D-pyranosyl-substituted phenyl compound according to claim 1, wherein:

X denotes hydrogen, fluorine, chlorine, $C_{1-6}$-alkyl, $C_{2-6}$-alkynyl, $C_{2-6}$-alkenyl, aminocarbonyl, hydroxycarbonyl, $C_{1-4}$-alkoxycarbonyl, $C_{1-6}$-alkylsulphonyl, amino, $C_{1-5}$-alkylamino, N—($C_{1-5}$-alkyl)-N—($C_{1-3}$-alkyl)-amino, mercapto or cyano, while alkyl groups may be partly or completely fluorinated or mono- or dichlorinated, and the aryl groups may independently of one another be mono- or disubstituted by identical or different groups L, where L is defined as in claim 1.

7. A D-pyranosyl-substituted phenyl compound according to claim 1, wherein:

X is hydrogen, chlorine, cyano, $C_{1-6}$-alkyl, $C_{2-6}$-alkynyl, $C_{2-6}$-alkenyl, $C_{1-6}$-alkylsulphonyl, hydroxycarbonyl, $C_{1-4}$-alkoxycarbonyl, aminocarbonyl or $C_{1-4}$-alkylaminocarbonyl, while alkyl groups may be mono- or polyfluorinated or monosubstituted by hydroxy or cyano.

8. A D-pyranosyl-substituted phenyl compound according to claim 1, wherein:

X is mercapto, $C_{1-5}$-alkylsulphanyl, $C_{2-5}$-alkenylsulphanyl, $C_{2-5}$-alkynylsulphanyl, $C_{3-7}$-cycloalkylsulphanyl or arylsulphanyl.

9. A D-pyranosyl-substituted phenyl compound according to claim 1 wherein:

X is amino, $C_{1-5}$-alkylamino, N—($C_{1-5}$-alkyl)-N—($C_{1-3}$-alkyl)-amino, $C_{1-4}$alkylcarbonylamino, N—($C_{1-5}$-alkyl)-N—(CN—($C_{1-4}$-alkylcarbonyl)-amino or arylamino.

10. A D-pyranosyl-substituted phenyl compound according to claim 1 wherein:

X is fluorine.

11. A D-pyranosyl-substituted phenyl compound according to claim 1 wherein:

the group X denotes bromine, iodine, $C_{1-6}$-alkylsulphonyloxy, arylsulphonyloxy or aryl-$C_{1-3}$-alkyl-sulphonyloxy.

12. A D-pyranosyl-substituted phenyl compound according to claim 1 wherein:

$R^2$ denotes hydrogen, fluorine, chlorine, bromine, methyl, hydroxy, methoxy, ethoxy, trifluoromethoxy, cyano, nitro or methyl substituted by 1 to 3 fluorine atoms.

13. A D-pyranosyl-substituted phenyl compound according to claim 1 wherein:

$R^4$ and $R^5$ independently of one another denote hydrogen or fluorine.

14. A D-pyranosyl-substituted phenyl compound according to claim 1 wherein: Z denotes oxygen or methylene.

15. A D-pyranosyl-substituted phenyl compound according to claim 1 wherein: $R^{7a}$, $R^{7b}$, $R^{7c}$ independently of one another denote hydrogen, ($C_{1-6}$-alkyl)oxycarbonyl, ($C_{1-8}$-alkyl)carbonyl or benzoyl.

16. A physiologically acceptable salt of a compound according to claim 1 with an inorganic or organic acid.

17. A pharmaceutical composition, comprised of a compound according to claim 1 optionally together with one or more inert carriers and/or diluents.

18. A method of treating a metabolic disorder in a patient wherein the metabolic disorder is selected from the list consisting of type 1 and type 2 diabetes mellitus, complications of diabetes, metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hypemricaemia by administration of a therapeutically effective amount of a compound according to claim 1 or a physiologically acceptable salt thereof.

19. A method of treating the degeneration of pancreatic beta cells and/or improving and/or restoring the functionality of pancreatic beta cells, said method comprised of the step of administering to a patient in need thereof therapeutically effective amount of a compound according to claim 1 or a physiologically acceptable salt thereof.

20. A D-pyranosyl-substituted phenyl compound of general formula I

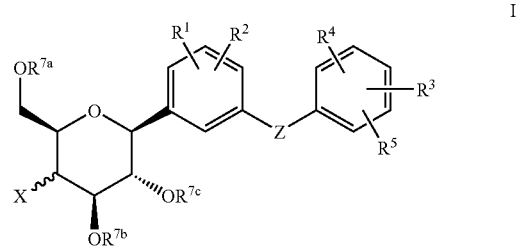

wherein:

$R^1$ denotes hydrogen, fluorine, chlorine, bromine, iodine, $C_{1-6}$-alkyl, $C_{2-6}$-alkynyl, $C_{2-6}$-alkenyl, $C_{3-10}$-cycloalkyl, $C_{3-10}$-cycloalkyl-$C_{1-3}$-alkyl, $C_{5-10}$-cycloalkenyl, $C_{5-10}$-cycloalkenyl-$C_{1-3}$-alkyl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1 -ylcarbonyl, morpholin-4-ylcarbonyl, piperazin-1-ylcarbonyl, 4-($C_{1-4}$-alkyl)piperazin-1-ylcarbonyl, $C_{1-4}$-alkoxycarbonyl, amino, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$-alkyl)piperazin-1-yl, $C_{1-4}$-alkylcarbonylamino, $C_{1-6}$-alkyloxy, $C_{3-10}$-cycloalkyloxy, $C_{5-10}$-cycloalkenyloxy, aryloxy, $C_{1-4}$alkylsulphanyl, $C_{1-4}$-alkylsulphinyl, $C_{1-4}$-alkylsulphonyl, $C_{3-10}$-cycloalkylsulphanyl, $C_{3-10}$-cycloalkylsulphinyl, $C_{3-10}$-cycloalkylsulphonyl, $C_{5-10}$-cycloalkenylsulphanyl, $C_{5-10}$-cycloalkenylsulphinyl, $C_{5-10}$-cycloalkenylsulphonyl, arylsulphanyl, arylsulphinylsulphinyl, arylsulphonyl, hydroxy, cyano or nitro, while alkyl, alkenyl, alkynyl, cycloalkyl and cycloalkenyl groups may be partly or completely fluorinated or may be mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be replaced by CO or $SO_2$ and $R^2$ denotes hydrogen, fluorine, chlorine, bromine, hydroxy, $C_{1-4}$-alkyl, $C_{1-4}$-alkoxy, cyano or nitro, while alkyl groups may be mono- or polysubstituted by fluorine, or in the event that $R^1$ and $R^2$ are bound to two adjacent C atoms of the phenyl ring, $R^1$ and $R^2$ may be joined together such that $R^1$ and $R^2$ together form a $C_{3-5}$-alkylene, $C_{3-5}$-alkenylene or butadienylene bridge, which may be partly or completely fluorinated or may be mono- or disubstituted by identical or different substituents selected from chlorine, hydroxy, $C_{1-3}$alkoxy and $C_{1-3}$-alkyl, and wherein one or two methylene groups may be replaced independently of one another by O, S, CO, SO, $SO_2$ or $NR^N$, and wherein in the case of a butadienylene bridge one or two methyne groups may be replaced by an N atom, $R^3$ denotes hydrogen, fluorine, chlorine, bromine, iodine, $C_{1-6}$-alkyl, $C_{2-6}$-alkynyl, $C_{2-6}$-alkenyl, $C_{3-10}$-cycloalkyl, $C_{3-10}$-Cycloalkyl-$C_{1-3}$-alkyl, $C_{5-10}$-cycloalkenyl, $C_{5-10}$-cycloalkenyl-$C_{1-3}$-alkyl, aryl, heteroaryl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperazin-1-ylcarbonyl, hydroxycarbonyl, $C_{1-4}$-alkoxycarbonyl, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$-alkyl)piperazin-1-yl, $C_{1-4}$-alkylcarbonylamino, arylcarbonylamino, heteroaryl-carbonylamino, $C_{1-4}$-alkysulphonylamino, arylsulphonylamino, $C_{1-6}$-alkoxy, $C_{3-7}$-cycloalkyloxy, $C_{5-7}$-cycloalkenyloxy, aryloxy, heteroaryloxy, $C_{1-4}$-alkyl-sulphanyl, $C_{1-4}$-alkylsulphinyl, $C_{1-4}$alkylsulphonyl, $C_{3-10}$-cycloalkylsulphanyl, $C_{3-10}$-cycloalkylsulphinyl, $C_{3-10}$cycloalkylsulphonyl, $C_{5-10}$-cycloalkenylsulphanyl, $C_{5-10}$-cycloalkenylsulphinyl, $C_{5-10}$-cyclo-alkenylsulphonyl, arylsulphanyl, arylsulphinyl, arylsulphonyl, amino, hydroxy, cyano or nitro, while alkyl, alkenyl, alkynyl, cycloalkyl- and cycloalkenyl groups may be partly or completely fluorinated or mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be substituted by CO or $SO_2$, and $R^4$ independently of one another denote hydrogen, fluorine, chlorine, bromine, iodine, cyano, nitro, $C_{1-3}$-alkyl, $C_{1-3}$-alkoxy or methyl or methoxy substituted by 1 to 3 fluorine atoms or if $R^3$ and $R^4$ are bound to two adjacent C atoms of the phenyl ring, $R^3$ and $R^4$ may be joined together such that $R^3$ and $R^4$ together form a $C_{3-5}$-alkylene, $C_{3-5}$-alkenylene or butadienylene bridge, which may be partly or completely fluorinated or mono- or disubstituted by identical or different substituents selected from chlorine, hydroxy, $C_{1-3}$-alkoxy and $C_{1-3}$-alkyl, and wherein one or two methylene groups may be replaced independently of one another by O, S, CO, SO, $SO_2$ or $NR^N$, and wherein in the case of a butadienylene bridge one or two methyne groups may be replaced by an N atom, $R^5$ independently of one another denote hydrogen, fluorine, chlorine, bromine, iodine, cyano, nitro, $C_{1-3}$-alkyl, $C_{1-3}$-alkoxy or methyl or methoxy substituted by 1 to 3 fluorine atoms, and $R^N$ denotes H, $C_{1-4}$-alkyl or $C_{1-4}$-alkylcarbonyl, L are selected independently of one another from among fluorine, chlorine, bromine, iodine, $C_{1-3}$-alkyl, difluoromethyl, trifluoromethyl, $C_{1-3}$-alkoxy, difluoromethoxy, trifluoromethoxy and cyano, $R^{7a}$, $R^{7b}$, $R^{7c}$ are each hydrogen, X denotes hydrogen, fluorine, chlorine, bromine, iodine, $C_{1-6}$-alkyl, $C_{2-6}$-alkynyl, $C_{2-6}$-alkenyl, $C_{3-7}$-cycloalkyl-$C_{1-3}$-alkyl, $C_{5-7}$-cycloalkenyl-$C_{1-3}$-alkyl, aryl-$C_{1-3}$-alkyl, heteroary-$_{1-3}$-alkyl, $C_{1-6}$-alkoxy, $C_{2-6}$-alkenyloxy, $C_{2-6}$-alkynyloxy, $C_{3-7}$-cycloalkyloxy, $C_{5-7}$-cycloalkenyloxy, aryloxy, heteroaryloxy, $C_{3-7}$-cycloalkyl-$C_{1-3}$-alkyloxy, $C_{5-7}$-cycloalkenyl-$C_{1-3}$-alkyloxy, aryl-$C_{1-3}$-alkyloxy, heteroaryl-$C_{1-3}$-alkyloxy, aminocarbonyl, $C_{1-4}$-alkylaminocarbonyl, di-($C_{1-3}$-alkyl)aminocarbonyl, hydroxycarbonyl, $C_{1-4}$-alkoxycarbonyl, aminocarbonyl-$C_{1-3}$-alkyl, $C_{1-4}$-alkylaminocarbonyl-$C_{1-3}$-alkyl, di-($C_{1-3}$-alkyl)aminocarbonyl-$C_{1-3}$-alkyl, hydroxycarbonyl-$C_{1-3}$-alkyl, $C_{1-4}$-alkoxycarbonyl-$C_{1-3}$-alkyl, $C_{3-7}$-cycloalkyloxy-$C_{1-3}$-alkyl, $C_{5-7}$-cycloalkenyloxy-$C_{1-3}$-alkyl, aryloxy-$C_{1-3}$-alkyl, heteroaryloxy-$C_{1-3}$-alkyl, $C_{1-4}$-alkylsulphonyloxy, arylsulphonyloxy, aryl-$C_{1-3}$-alkyl-sulphonyloxy or cyano, while a methylene group directly linked to the pyranose ring may be replaced by $NR^N$, S, CO, SO or $SO_2$, and the alkyl, alkenyl, alkynyl, cycloalkyl and cycloalkenyl groups therein may be partly or completely fluorinated or mono- or disubstituted by identical or different substituents selected from chlorine, cyano, hydroxy, $C_{1-3}$-alkoxy, $C_{1-3}$-alkylsulphanyl, —$NH_2$, —$NHR^N$, —$NR^N$($C_{1-3}$-alkyl) and $C_{1-3}$-alkyl, and in the cycloalkyl and cycloalkenyl groups therein one or two methylene groups may be replaced independently of one another by O, S, CO, SO or $SO_2$, and Z denotes oxygen, methylene, dimethylmethylene, 1,1-cyclopropylene, difluoromethylene or carbonyl;

while by the aryl groups mentioned in the definition of the above-mentioned groups are meant phenyl or naphthyl groups, which may be mono- or disubstituted independently of one another by identical or different groups L; and by the heteroaryl groups mentioned in the definition of the above-mentioned groups are meant a pyrrolyl, furanyl, thienyl, pyridyl, indolyl, benzofuranyl, benzothiophenyl, qiuinolinyl or isoguinolinyl group, or a pyrrolyl, furanyl, thienyl or pyridyl group, wherein one or two methyne groups are replaced by nitrogen atoms, or an indolyl, benzofuranyl, benzothiophenyl, qiuinolinyl or isoquinolinyl group, wherein one to three methyne groups are replaced by nitrogen atoms, while the above-mentioned heteroaryl groups may independently of one another be mono- or disubstituted by identical or different groups L;

while by the N-heterocycloalkyl group mentioned in the definition of the above-mentioned groups is meant a saturated carbocyclic ring which comprises an imino group in the ring, which may comprise a further imino group or an O or S atom in the ring, and unless otherwise stated, the above-mentioned alkyl groups may be straight-chain or branched, the tautomers, the mixtures thereof and the physiologically acceptable salts thereof.

21. A D-pyranosyl-substituted phenyl compound of general formula IB

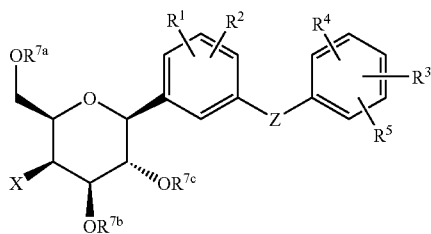

wherein:
- $R^1$ denotes hydrogen, fluorine, chlorine, bromine, iodine, $C_{1-6}$-alkyl, $C_{2-6}$-alkynyl, $C_{2-6}$-alkenyl, $C_{3-10}$-cycloalkyl, $C_{3-10}$-cycloalkyl-$C_{1-3}$-alkyl, $C_{5-10}$-cycloalkenyl, $C_{5-10}$-cycloalkenyl-$C_{1-3}$-alkyl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperazin-1-ylcarbonyl, $C_{1-4}$-alkoxycarbonyl, amino, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$-alkyl)piperazin-1-yl, $C_{1-4}$-alkylcarbonylamino, $C_{1-6}$-alkyloxy, $C_{3-10}$-cycloalkyloxy, $C_{5-10}$-cycloalkenyloxy, aryloxy, $C_{1-4}$-alkylsulphanyl, $C_{1-4}$-alkylsulphinyl, $C_{1-4}$-alkylsulphonyl, $C_{3-10}$-cycloalkylsulphanyl, $C_{3-10}$-cycloalkylsulphinyl, $C_{3-10}$-cycloalkylsulphonyl, $C_{5-10}$-cycloalkenylsulphanyl, $C_{5-10}$-cycloalkenylsulphinyl, $C_{5-10}$-cycloalkenylsulphonyl, arylsulphanyl, arylsulphinyl, arylsulphonyl, hydroxy, cyano or nitro,
  while alkyl, alkenyl, alkynyl, cycloalkyl and cycloalkenyl groups may be partly or completely fluorinated or may be mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and
in N-heterocycloalkyl groups a methylene group may be replaced by CO or $SO_2$, and
- $R^2$ denotes hydrogen, fluorine, chlorine, bromine, hydroxy, $C_{1-4}$-alkyl, $C_{1-4}$-alkoxy, cyano or nitro, while alkyl groups may be mono- or polysubstituted by fluorine, or in the event that $R^1$ and $R^2$ are bound to two adjacent C atoms of the phenyl ring, $R^1$ and $R^2$ may be joined together such that $R^1$ and $R^2$ together form a $C_{3-5}$-alkylene, $C_{3-5}$-alkenylene or butadienylene bridge, which may be partly or completely fluorinated or may be mono- or disubstituted by identical or different substituents selected from chlorine, hydroxy, $C_{1-3}$-alkoxy and $C_{1-3}$-alkyl, and wherein one or two methylene groups may be replaced independently of one another by O, S, CO, SO, $SO_2$ or $NR^N$, and wherein in the case of a butadienylene bridge one or two methyne groups may be replaced by an N atom,
- $R^3$ denotes hydrogen, fluorine, chlorine, bromine, iodine, $C_{1-6}$-alkyl, $C_{2-6}$-alkynyl, $C_{2-6}$-alkenyl, $C_{3-10}$-cycloalkyl, $C_{3-10}$-Cycloalkyl-$C_{1-3}$-alkyl, $C_{5-10}$-cycloalkenyl, $C_{5-10}$-cycloalkenyl-$C_{1-3}$-alkyl, aryl, heteroaryl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperazin-1-ylcarbonyl, hydroxycarbonyl, $C_{1-4}$-alkoxycarbonyl, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$-alkyl)piperazin-1-yl, $C_{1-4}$-alkylcarbonylamino, arylcarbonylamino, heteroaryl-carbonylamino, $C_{1-4}$-alkylsulphonylamino, arylsulphonylamino, $C_{1-6}$-alkoxy, $C_{3-7}$-cycloalkyloxy, $C_{5-7}$-cycloalkenyloxy, aryloxy, heteroaryloxy, $C_{1-4}$-alkyl-sulphanyl, $C_{1-4}$-alkylsulphinyl, $C_{1-4}$-alkylsulphonyl, $C_{3-10}$-cycloalkylsulphanyl, $C_{3-10}$-cycloalkylsulphinyl, $C_{3-10}$-cycloalkylsulphonyl, $C_{5-10}$-cycloalkenylsulphanyl, $C_{5-10}$-cycloalkenylsulphinyl, $C_{5-10}$-cycloalkenylsulphonyl, arylsulphanyl, arylsulphinyl, arylsulphonyl, amino, hydroxy, cyano or nitro,
  while alkyl, alkenyl, alkynyl, cycloalkyl- and cycloalkenyl groups may be partly or completely fluorinated or mono- or disubstituted by identical or different substituents selected from chlorine, hydroxy, $C_{1-3}$-alkoxy and $C_{1-3}$-alkyl, and
  in cycloalkyl and cycloalkenyl groups one or two methylene groups may be replaced independently of one another by O, S, CO, SO or $SO_2$, and
  in N-heterocycloalkyl groups a methylene group may be substituted by CO or $S0_2$, and
- $R^4$ independently of one another denote hydrogen, fluorine, chlorine, bromine, iodine, cyano, nitro, $C_{1-3}$-alkyl, $C_{1-3}$-alkoxy or methyl or methoxy substituted by 1 to 3 fluorine atoms, or
  if $R^3$ and $R^4$ are bound to two adjacent C atoms of the phenyl ring, $R^3$ and $R^4$ may be joined together such that $R^3$ and $R^4$ together form a $C_{3-5}$-alkylene, $C_{3-5}$-alkenylene or butadienylene bridge, which may be partly or completely fluorinated or mono- or disubstituted by identical or different substituents selected from chlorine, hydroxy, $C_{1-3}$-alkoxy and $C_{1-3}$-alkyl, and wherein one or two methylene groups may be replaced independently of one another by O, S, CO, SO, $SO_2$ or $NR^N$, and wherein in the case of a butadienylene bridge one or two methyne groups may be replaced by an N atom,
- $R^5$ independently of one another denote hydrogen, fluorine, chlorine, bromine, iodine, cyano, nitro, $C_{1-3}$-alkyl, $C_{1-3}$-alkoxy or methyl or methoxy substituted by 1 to 3 fluorine atoms, and
- $R^N$ denotes H, $C_{1-4}$-alkyl or $C_{1-4}$-alkylcarbonyl,
- L are selected independently of one another from among fluorine, chlorine, bromine, iodine, $C_{1-3}$-alkyl, difluoromethyl, trifluoromethyl, $C_{1-3}$-alkoxy, difluoromethoxy, trifluoromethoxy and cyano,
- $R^{7a}$, $R^{7b}$, $R^{7c}$ independently of one another have a meaning selected from among hydrogen, ($C_{1-18}$-alkyl)carbonyl, ($C_{1-18}$-alkyl)oxycarbonyl, arylcarbonyl and aryl-($C_{1-3}$-alkyl)-carbonyl,
- X denotes hydrogen, fluorine, chlorine, bromine, iodine, $C_{1-6}$-alkyl, $C_{2-6}$-alkynyl, $C_{2-6}$-alkenyl, $C_{3-7}$-cycloalkyl-$C_{1-3}$-alkyl, $C_{5-7}$-cycloalkenyl-$C_{1-3}$-alkyl, aryl-$C_{1-3}$-alkyl, heteroaryl-$C_{1-3}$-alkyl, $C_{1-6}$-alkoxy, $C_{2-6}$-alkenyloxy, $C_{2-6}$-alkynyloxy, $C_{3-7}$-cycloalkyloxy, $C_{5-7}$-cycloalkenyloxy, aryloxy, heteroaryloxy, $C_{3-7}$-cycloalkyl-$C_{1-3}$-alkyloxy, $C_{5-7}$-cycloalkenyl-$C_{1-3}$-alkyloxy, aryl-$C_{1-3}$-alkyloxy, heteroaryl-$C_{1-3}$-alkyloxy, aminocarbonyl, $C_{1-4}$-alkylaminocarbonyl, di-($C_{1-3}$-alkyl)aminocarbonyl, hydroxycarbonyl, $C_{1-4}$-alkoxycarbonyl, aminocarbonyl-$C_{1-3}$-alkyl, $C_{1-4}$-alkylaminocarbonyl-$C_{1-3}$-alkyl, di-($C_{1-3}$-alkyl)aminocarbonyl-$C_{1-3}$-alkyl, hydroxycarbonyl-$C_{1-3}$-alkyl, $C_{1-4}$- alkoxycarbonyl-$C_{1-3}$-alkyl, $C_{3-7}$-cycloalkyloxy-$C_{1-3}$-alkyl, $C_{5-7}$-cycloalkenyloxy-$C_{1-3}$-alkyl, aryloxy-$C_{1-3}$-alkyl, heteroaryloxy-$C_{1-3}$-alkyl, $C_{1-4}$-alkylsulphonyloxy, arylsulphonyloxy, aryl-$C_{1-3}$-alkyl-sulphonyloxy or cyano, while a methylene group directly linked to the pyranose ring may be replaced by $NR^N$, S, CO, SO or $SO_2$, and alkyl, alkenyl, alkynyl, cycloalkyl and cycloalkenyl groups may be partly or completely fluorinated or mono- or disubstituted by identical or different substituents selected from chlorine, cyano, hydroxy, $C_{1-3}$-alkoxy, $C_{1-3}$-alkylsulphanyl, $-NH_2$, $-NHR^N$, $-NR^N(C_{1-3}$-alkyl) and $C_{1-3}$-alkyl, and in cycloalkyl and cycloalkenyl groups one or two methylene groups may be replaced independently of one another by O, S, CO, SO or $SO_2$, and Z denotes oxygen, methylene, dimethylmethylene, 1,1-cyclopropylene, difluoromethylene or carbonyl;

while by the aryl groups mentioned in the definition of the above-mentioned groups are meant phenyl or naphthyl groups, which may be mono- or disubstituted independently of one another by identical or different groups L; and by the heteroaryl groups mentioned in the definition of the above-mentioned groups are meant a pyrrolyl, furanyl, thienyl, pyridyl, indolyl, benzofuranyl, benzothiophenyl, quinolinyl or isoquinolinyl group, or a pyrrolyl, furanyl, thienyl or pyridyl group, wherein one or two methyne groups are replaced by nitrogen atoms, or an indolyl, benzofuranyl, benzothiophenyl, quinolinyl or isoquinolinyl group, wherein one to three methyne groups are replaced by nitrogen atoms, while the above-mentioned heteroaryl groups may independently of one another be mono- or disubstituted by identical or different groups L;

while by the N-heterocycloalkyl group mentioned in the definition of the above-mentioned groups is meant a saturated carbocyclic ring which comprises an imino group in the ring, which may comprise a further imino group or an O or S atom in the ring, and unless otherwise stated, the above-mentioned alkyl groups may be straight-chain or branched, the tautomers, the mixtures thereof and the physiologically acceptable salts thereof.

22. A pharmaceutical composition, comprised of a compound according to claim 20 optionally together with one or more inert carriers and/or diluents.

23. A pharmaceutical composition, comprised of a compound according to claim 21 optionally together with one or more inert carriers and/or diluents.

24. A pharmaceutical composition, comprised of a compound of general formula I

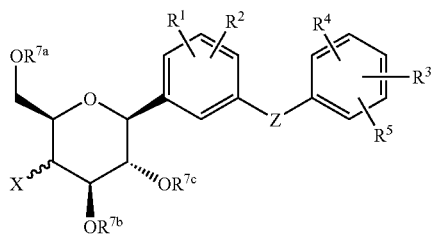

I wherein:
$R^1$ denotes hydrogen, fluorine, chlorine, bromine, iodine, $C_{1-6}$-alkyl, $C_{2-6}$-alkynyl, $C_{2-6}$-alkenyl, $C_{3-10}$-cycloalkyl, $C_{3-10}$-cycloalkyl-$C_{1-3}$-alkyl, $C_{5-10}$-cycloalkenyl, $C_{5-10}$-cycloalkenyl-$C_{1-3}$-alkyl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperazin-1-ylcarbonyl, $C_{1-4}$-alkoxycarbonyl, amino, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$-alkyl)piperazin-1-yl, $C_{1-4}$-alkylcarbonylamino, $C_{1-6}$-alkyloxy, $C_{3-10}$-cycloalkyloxy, $C_{5-10}$-cycloalkenyloxy, aryloxy, $C_{1-4}$-alkylsulphanyl, $C_{1-4}$-alkylsulphinyl, $C_{1-4}$-alkylsulphonyl, $C_{3-10}$-cycloalkylsulphanyl, $C_{3-10}$-cycloalkylsulphinyl, $C_{3-10}$-cycloalkylsulphonyl, $C_{5-10}$-cycloalkenylsulphanyl, $C_{5-10}$-cycloalkenylsulphinyl, $C_{5-10}$-cycloalkenylsulphonyl, arylsulphanyl, arylsulphinyl, arylsulphonyl, hydroxy, cyano or nitro, while alkyl, alkenyl, alkynyl, cycloalkyl and cycloalkenyl groups may be partly or completely fluorinated or may be mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be replaced by CO or $SO_2$, and $R^2$ denotes hydrogen, fluorine, chlorine, bromine, hydroxy, $C_{1-4}$-alkyl, $C_{1-4}$-alkoxy, cyano or nitro, while alkyl groups may be mono- or polysubstituted by fluorine, or in the event that $R^1$ and $R^2$ are bound to two adjacent C atoms of the phenyl ring, $R^1$ and $R^2$ may be joined together such that $R^1$ and $R^2$ together form a $C_{3-5}$-alkylene, $C_{3-5}$-alkenylene or butadienylene bridge, which may be partly or completely fluorinated or may be mono- or disubstituted by identical or different substituents selected from chlorine, hydroxy, $C_{1-3}$-alkoxy and $C_{1-3}$-alkyl, and wherein one or two methylene groups may be replaced independently of one another by O, S, CO, SO, $SO_2$ or $NR^N$, and wherein in the case of a butadienylene bridge one or two methyne groups may be replaced by an N atom, $R^3$ denotes hydrogen, fluorine, chlorine, bromine, iodine, $C_{1-6}$-alkyl, $C_{2-6}$-alkynyl, $C_{2-6}$-alkenyl, $C_{3-10}$-cycloalkyl, $C_{3-10}$-Cycloalkyl-$C_{1-3}$-alkyl, $C_{5-10}$-cycloalkenyl, $C_{5-10}$-cycloalkenyl-$C_{1-3}$-alkyl, aryl, heteroaryl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperazin-1-ylcarbonyl, hydroxycarbonyl, $C_{1-4}$-alkoxycarbonyl, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$-alkyl)piperazin-1-yl, $C_{1-4}$-alkylcarbonylamino, arylcarbonylamino, heteroaryl-carbonylamino, $C_{1-4}$-alkylsulphonylamino, arylsulphonylamino, $C_{1-6}$-alkoxy, $C_{3-7}$-cycloalkyloxy, $C_{5-7}$-cycloalkenyloxy, aryloxy, heteroaryloxy, $C_{1-4}$-alkyl-sulphanyl, $C_{1-4}$-alkylsulphinyl, $C_{1-4}$-alkylsulphonyl, $C_{3-10}$-cycloalkylsulphanyl, $C_{3-10}$-cycloalkylsulphinyl, $C_{3-10}$-cycloalkylsulphonyl, $C_{5-10}$-cycloalkenylsulphanyl, $C_{5-10}$-cycloalkenylsulphinyl, $C_{5-10}$-cycloalkenylsulphonyl, arylsulphanyl, arylsulphinyl, arylsulphonyl, amino, hydroxy, cyano or nitro, while alkyl, alkenyl, alkynyl, cycloalkyl- and cycloalkenyl groups may be partly or completely fluorinated or mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be substituted by CO or $SO_2$, and $R^4$ independently of one another denote hydrogen, fluorine, chlorine, bromine, iodine, cyano, nitro, $C_{1-3}$-alkyl, $C_{1-3}$-alkoxy or methyl or methoxy substituted by 1 to 3 fluorine atoms, or if $R^3$ and $R^4$ are bound to two adjacent C atoms of the phenyl ring, $R^3$ and $R^4$ may be joined together such that $R^3$ and $R^4$ together form a $C_{3-5}$-alkylene, $C_{3-5}$-alkenylene or butadienylene bridge, which may be partly or completely fluorinated or mono- or disubstituted by identical or different substituents selected from chlorine, hydroxy, $C_{1-3}$-alkoxy and $C_{1-3}$-alkyl, and wherein one or two methylene groups may be replaced independently of one another by O, S, CO, SO, $SO_2$ or $NR^N$, and wherein in the case of a butadienylene bridge one or two methyne groups may be replaced by an N atom, $R^5$ independently of one another denote hydrogen, fluorine, chlorine, bromine, iodine, cyano, nitro, $C_{1-3}$-alkyl, $C_{1-3}$-alkoxy or methyl or methoxy substituted by 1 to 3 fluorine atoms, and $R^N$ denotes H, $C_{1-4}$-alkyl or $C_{1-4}$-alkylcarbonyl, L are selected independently of one another from among fluorine, chlorine, bromine, iodine, $C_{1-3}$-alkyl, difluoromethyl, trifluoromethyl, $C_{1-3}$-alkoxy, difluoromethoxy, trifluoromethoxy and cyano, $R^{7a}$, $R^{7b}$, $R^{7c}$ independently of one another have a meaning selected from among hydrogen, ($C_{1-18}$-alkyl)carbonyl, ($C_{1-18}$-alkyl)oxycarbonyl, arylcarbonyl and aryl-($C_{1-3}$-alkyl)-carbonyl, X denotes hydrogen, fluorine, chlorine, bromine, iodine, $C_{1-6}$-alkyl, $C_{2-6}$-alkynyl, $C_{3-7}$-cycloalkyl-$C_{1-3}$-alkyl, $C_{5-7}$-cycloalkenyl-$C_{1-3}$-alkyl, aryl-$C_{1-3}$-alkyl, heteroaryl-$C_{1-3}$-alkyl, $C_{1-6}$-alkoxy, $C_{2-6}$-alkenyloxy, $C_{2-6}$-alkynyloxy, $C_{3-7}$-cycloalkyloxy, $C_{5-7}$-cycloalkenyloxy, aryloxy, heteroaryloxy, $C_{3-7}$-cycloalkyl-$C_{1-3}$-alkyloxy, $C_{5-7}$-cycloalkenyl-$C_{1-3}$-alkyloxy, aryl-$C_{1-3}$-alkyloxy, heteroaryl-$C_{1-3}$-alkyloxy, aminocarbonyl, $C_{1-4}$-alkylaminocarbonyl, di-($C_{1-3}$-alkyl)aminocarbonyl, hydroxycarbonyl, $C_{1-4}$-alkoxycarbonyl, aminocarbonyl-$C_{1-3}$-alkyl, $C_{1-4}$-alkylaminocarbonyl-$C_{1-3}$-alkyl, di-($C_{1-3}$-alkyl)aminocarbonyl-$C_{1-3}$-alkyl, hydroxycarbonyl-$C_{1-3}$-alkyl, $C_{1-4}$-alkoxycarbonyl-$C_{1-3}$-alkyl, $C_{3-7}$-cycloalkyloxy-$C_{1-3}$-alkyl, $C_{5-7}$-cycloalkenyloxy-$C_{1-3}$-alkyl, aryloxy-$C_{1-3}$-alkyl, heteroaryloxy-$C_{1-3}$-alkyl, $C_{1-4}$-alkylsulphonyloxy, arylsulphonyloxy, aryl-$C_{1-3}$-alkyl-sulphonyloxy or cyano, while a methylene group directly linked to the pyranose ring may be replaced by $NR^N$, S, CO, SO or $SO_2$, and alkyl, alkenyl, alkynyl, cycloalkyl and cycloalkenyl groups may be partly or completely fluorinated or mono- or disubstituted by identical or different substituents selected from chlorine, cyano, hydroxy, $C_{1-3}$-alkoxy, $C_{1-3}$-alkylsulphanyl, $-NH_2$, $-NHR^N$, $-NR^N(C_{1-3}$-alkyl) and $C_{1-3}$-alkyl, and in cycloalkyl and cycloalkenyl groups one or two methylene groups may be replaced independently of one another by O, S, CO, SO or $SO_2$, and Z denotes oxygen, methylene, dimethylmethylene, 1,1-cyclopropylene, difluoromethylene or carbonyl;

while by the aryl groups mentioned in the definition of the above-mentioned groups are meant phenyl or naphthyl groups, which may be mono- or disubstituted independently of one another by identical or different groups L; and by the heteroaryl groups mentioned in the definition of the above-mentioned groups are meant a pyrrolyl, furanyl, thienyl, pyridyl, indolyl, benzofuranyl, benzothiophenyl, quinolinyl or isoquinolinyl group, or a pyrrolyl, furanyl, thienyl or pyridyl group, wherein one or two methyne groups are replaced by nitrogen atoms, or an indolyl, benzofuranyl, benzothiophenyl, quinolinyl or isoquinolinyl group, wherein one to three methyne groups are replaced by nitrogen atoms, while the above-mentioned heteroaryl groups may independently of one another be mono- or disubstituted by identical or different groups L;

while by the N-heterocycloalkyl group mentioned in the definition of the above-mentioned groups is meant a saturated carbocyclic ring which comprises an imino group in the ring, which may comprise a further imino group or an O or S atom in the ring, and unless otherwise stated, the above-mentioned alkyl groups may be straight-chain or branched, the tautomers, the mixtures thereof and the physiologically acceptable salts thereof, together with one or more inert carriers and/or diluents.

25. A method of treating a metabolic disorder in a patient wherein the metabolic disorder is selected from the list consisting of type 1 and type 2 diabetes mellitus, complications of diabetes, metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hypemricaemia by administration of a therapeutically effective amount of a compound according to claim 20 or a physiologically acceptable salt thereof.

26. A method of treating the degeneration of pancreatic beta cells and/or improving and/or restoring the functionality of pancreatic beta cells, said method comprised of the step of administering to a patient in need thereof therapeutically effective amount of a compound according to claim 20 or a physiologically acceptable salt thereof.

27. A method of treating a metabolic disorder in a patient wherein the metabolic disorder is selected from the list consisting of type 1 and type 2 diabetes mellitus, complications of diabetes, metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hypemricaemia by administration of a therapeutically effective amount of a compound according to claim 21 or a physiologically acceptable salt thereof.

28. A method of treating the degeneration of pancreatic beta cells and/or improving and/or restoring the functionality of pancreatic beta cells, said method comprised of the step of administering to a patient in need thereof therapeutically effective amount of a compound according to claim 21 or a physiologically acceptable salt thereof.

* * * * *